(12) United States Patent
el Kaliouby et al.

(10) Patent No.: US 10,779,761 B2
(45) Date of Patent: *Sep. 22, 2020

(54) SPORADIC COLLECTION OF AFFECT DATA WITHIN A VEHICLE

(71) Applicant: Affectiva, Inc., Boston, MA (US)

(72) Inventors: Rana el Kaliouby, Milton, MA (US); Abdelrahman N. Mahmoud, Somerville, MA (US); Seyedmohammad Mavadati, Watertown, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/208,211

(22) Filed: Dec. 3, 2018

(65) Prior Publication Data

US 2019/0133510 A1    May 9, 2019

Related U.S. Application Data

(63) Continuation-in-part of application No. 15/875,644, filed on Jan. 19, 2018, now Pat. No. 10,627,817, (Continued)

(51) Int. Cl.
*A61B 5/16* (2006.01)
*G08G 1/0967* (2006.01)
(Continued)

(52) U.S. Cl.
CPC ............ *A61B 5/165* (2013.01); *A61B 5/0022* (2013.01); *A61B 5/0077* (2013.01); *A61B 5/168* (2013.01);
(Continued)

(58) Field of Classification Search
USPC .......................................................... 701/36
See application file for complete search history.

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Tyler D Paige
(74) *Attorney, Agent, or Firm* — Adams Intellex, PLC

(57) ABSTRACT

Mental state analysis uses sporadic collection of affect data within a vehicle. Mental state data of a vehicle occupant is collected within a vehicle on an intermittent basis. The mental state data includes facial image data and the facial image data is collected intermittently across a plurality of devices within the vehicle. The mental state data further includes audio information. Processors are used to interpolate mental state data in between the collecting which is intermittent. Analysis of the mental state data is obtained on the vehicle occupant, where the analysis of the mental state data includes analyzing the facial image data. An output is rendered based on the analysis of the mental state data. The rendering includes communicating by a virtual assistant, communicating with a navigation component, and manipulating the vehicle. The mental state data is translated into an emoji.

27 Claims, 19 Drawing Sheets

Related U.S. Application Data which is a continuation-in-part of application No. 15/273,765, filed on Sep. 23, 2016, now abandoned, application No. 16/208,211, which is a continuation-in-part of application No. 14/961,279, filed on Dec. 7, 2015, now Pat. No. 10,143,414, which is a continuation-in-part of application No. 14/796,419, filed on Jul. 10, 2015, now abandoned, said application No. 15/273,765 is a continuation-in-part of application No. 14/796,419, filed on Jul. 10, 2015, now abandoned, which is a continuation-in-part of application No. 14/460,915, filed on Aug. 15, 2014, said application No. 14/961,279 is a continuation of application No. 14/064,136, filed on Oct. 26, 2013, now Pat. No. 9,204,836, which is a continuation-in-part of application No. 13/153,745, filed on Jun. 6, 2011, now abandoned, said application No. 14/460,915 is a continuation-in-part of application No. 13/153,745, filed on Jun. 6, 2011, now abandoned.

(60) Provisional application No. 62/611,780, filed on Dec. 29, 2017, provisional application No. 62/593,449, filed on Dec. 1, 2017, provisional application No. 62/593,440, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/844,478, filed on Jul. 10, 2013, provisional application No. 61/789,038, filed on Mar. 15, 2013, provisional application No. 61/793,761, filed on Mar. 15, 2013, provisional application No. 61/790,461, filed on Mar. 15, 2013, provisional application No. 61/798,731, filed on Mar. 15, 2013, provisional application No. 61/747,810, filed on Dec. 31, 2012, provisional application No. 61/747,651, filed on Dec. 31, 2012, provisional application No. 61/719,383, filed on Oct. 27, 2012, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.
| | |
|---|---|
| *B60W 40/08* | (2012.01) |
| *G06K 9/00* | (2006.01) |
| *G06N 7/00* | (2006.01) |
| *A61B 5/00* | (2006.01) |
| *A61B 5/18* | (2006.01) |
| *G06N 3/04* | (2006.01) |
| *G06N 3/08* | (2006.01) |
| *G08G 1/01* | (2006.01) |
| *G06N 20/10* | (2019.01) |
| *G06N 3/00* | (2006.01) |
| *G06K 9/62* | (2006.01) |
| *G10L 25/63* | (2013.01) |
| *A61B 5/053* | (2006.01) |
| *G06Q 30/02* | (2012.01) |
| *A61B 5/11* | (2006.01) |
| *A61B 5/08* | (2006.01) |
| *A61B 5/024* | (2006.01) |
| *A61B 5/0205* | (2006.01) |
| *A61B 5/01* | (2006.01) |

(52) U.S. Cl.
CPC ............... *A61B 5/18* (2013.01); *B60W 40/08* (2013.01); *G06K 9/00315* (2013.01); *G06K 9/6273* (2013.01); *G06N 3/006* (2013.01); *G06N 3/0454* (2013.01); *G06N 3/084* (2013.01); *G06N 7/005* (2013.01); *G06N 20/10* (2019.01); *G08G 1/0112* (2013.01); *G08G 1/0129* (2013.01); *G08G 1/096716* (2013.01); *G08G 1/096725* (2013.01); *G08G 1/096741* (2013.01); *G08G 1/096775* (2013.01); *G10L 25/63* (2013.01); *A61B 5/01* (2013.01); *A61B 5/0205* (2013.01); *A61B 5/02055* (2013.01); *A61B 5/02405* (2013.01); *A61B 5/0531* (2013.01); *A61B 5/0533* (2013.01); *A61B 5/08* (2013.01); *A61B 5/11* (2013.01); *A61B 5/6898* (2013.01); *A61B 5/72* (2013.01); *G06Q 30/0271* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |

(56) References Cited

U.S. PATENT DOCUMENTS

| | | | |
|---|---|---|---|
| 5,760,917 A | 6/1998 | Sheridan | |
| 5,762,611 A | 6/1998 | Lewis et al. | |
| 5,772,508 A | 6/1998 | Sugita et al. | |
| 5,772,591 A | 6/1998 | Cram | |
| 5,774,591 A * | 6/1998 | Black | G06K 9/00248 382/118 |
| 5,802,220 A * | 9/1998 | Black | G06K 9/00248 382/100 |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,091,334 A | 7/2000 | Galiana et al. | |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,606,102 B1 | 8/2003 | Odom | |
| 6,629,104 B1 | 9/2003 | Parulski et al. | |
| 6,724,920 B1 | 4/2004 | Berenz et al. | |
| 6,792,458 B1 | 9/2004 | Muret et al. | |
| 6,847,376 B2 | 1/2005 | Engeldrum et al. | |
| 7,003,135 B2 | 2/2006 | Hsieh et al. | |
| 7,013,478 B1 | 3/2006 | Hendricks et al. | |
| 7,027,621 B1 | 4/2006 | Prokoski | |
| 7,110,570 B1 | 9/2006 | Berenz et al. | |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,319,779 B1 | 1/2008 | Mummareddy et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,757,171 B1 | 7/2010 | Wong et al. | |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1 | 4/2011 | Sharma | |
| 8,010,458 B2 | 8/2011 | Galbreath et al. | |
| 8,022,831 B1 | 9/2011 | Wood-Eyre | |
| 8,219,438 B1 | 7/2012 | Moon et al. | |
| 8,300,891 B2 | 10/2012 | Chen et al. | |
| 8,369,608 B2 | 2/2013 | Gunaratne | |
| 8,401,248 B1 | 3/2013 | Moon et al. | |
| 8,442,638 B2 | 5/2013 | Libbus et al. | |
| 8,522,779 B2 | 9/2013 | Lee et al. | |
| 8,600,120 B2 | 12/2013 | Gonion et al. | |
| 8,640,021 B2 | 1/2014 | Perez et al. | |
| 8,738,523 B1 | 5/2014 | Sanchez et al. | |
| 8,947,217 B2 | 2/2015 | Moussa et al. | |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0093784 A1 | 5/2003 | Dimitrova et al. | |
| 2003/0182123 A1 | 9/2003 | Mitsuyoshi | |
| 2003/0191682 A1 | 10/2003 | Shepard et al. | |
| 2003/0191816 A1 | 10/2003 | Landress et al. | |
| 2004/0181457 A1 | 9/2004 | Biebesheimer | |
| 2005/0187437 A1 | 8/2005 | Matsugu | |
| 2005/0283055 A1 | 12/2005 | Shirai et al. | |
| 2005/0289582 A1 | 12/2005 | Tavares et al. | |
| 2006/0011399 A1 * | 1/2006 | Brockway | A61B 5/18 180/272 |
| 2006/0019224 A1 | 1/2006 | Behar et al. | |
| 2006/0143647 A1 | 6/2006 | Bill | |
| 2006/0149428 A1 | 7/2006 | Kim et al. | |
| 2006/0170945 A1 | 8/2006 | Bill | |
| 2006/0235753 A1 | 10/2006 | Kameyama | |
| 2007/0167689 A1 | 7/2007 | Ramadas et al. | |
| 2007/0173733 A1 | 7/2007 | Le et al. | |
| 2007/0239787 A1 | 10/2007 | Cunningham et al. | |
| 2007/0255831 A1 | 11/2007 | Hayashi et al. | |
| 2007/0265507 A1 | 11/2007 | de Lemos | |
| 2007/0299964 A1 | 12/2007 | Wong et al. | |
| 2008/0059570 A1 | 3/2008 | Bill | |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0184170 A1 | 7/2008 | Periyalwar | |
| 2008/0208015 A1 | 8/2008 | Morris et al. | |
| 2008/0221472 A1 | 9/2008 | Lee et al. | |
| 2008/0287821 A1 | 11/2008 | Jung et al. | |
| 2008/0292151 A1 | 11/2008 | Kurtz et al. | |
| 2009/0002178 A1 | 1/2009 | Guday et al. | |
| 2009/0006206 A1 | 1/2009 | Groe | |
| 2009/0083421 A1 | 3/2009 | Glommen et al. | |
| 2009/0094286 A1 | 4/2009 | Lee et al. | |
| 2009/0112694 A1 | 4/2009 | Jung et al. | |
| 2009/0112810 A1 | 4/2009 | Jung et al. | |
| 2009/0133048 A1 | 5/2009 | Gibbs et al. | |
| 2009/0149721 A1 | 6/2009 | Yang | |
| 2009/0150919 A1 | 6/2009 | Lee et al. | |
| 2009/0156907 A1 | 6/2009 | Jung et al. | |
| 2009/0164132 A1 | 6/2009 | Jung et al. | |
| 2009/0193344 A1 | 7/2009 | Smyers | |
| 2009/0209829 A1 | 8/2009 | Yanagidaira et al. | |
| 2009/0210290 A1 | 8/2009 | Elliott et al. | |
| 2009/0217315 A1 | 8/2009 | Malik et al. | |

(56) References Cited

U.S. PATENT DOCUMENTS

| | | | |
|---|---|---|---|
| 2009/0226043 A1* | 9/2009 | Angell | G06K 9/00771 382/115 |
| 2009/0259518 A1 | 10/2009 | Harvey | |
| 2009/0270170 A1 | 10/2009 | Patton | |
| 2009/0271417 A1 | 10/2009 | Toebes et al. | |
| 2009/0299840 A1 | 12/2009 | Smith | |
| 2010/0070523 A1 | 3/2010 | Delgo et al. | |
| 2010/0099955 A1 | 4/2010 | Thomas et al. | |
| 2010/0123588 A1* | 5/2010 | Cruz Hernandez | A61B 5/02438 340/573.1 |
| 2010/0134302 A1 | 6/2010 | Ahn et al. | |
| 2010/0266213 A1 | 10/2010 | Hill | |
| 2010/0274847 A1 | 10/2010 | Anderson et al. | |
| 2010/0324437 A1 | 12/2010 | Freeman | |
| 2011/0083075 A1* | 4/2011 | MacNeille | B60K 37/06 715/728 |
| 2011/0126226 A1 | 5/2011 | Makhlouf | |
| 2011/0134026 A1 | 6/2011 | Kang et al. | |
| 2011/0143728 A1 | 6/2011 | Holopainen et al. | |
| 2011/0144971 A1 | 6/2011 | Danielson | |
| 2011/0196855 A1 | 8/2011 | Wable et al. | |
| 2011/0231240 A1 | 9/2011 | Schoen et al. | |
| 2011/0251493 A1 | 10/2011 | Poh et al. | |
| 2011/0263946 A1 | 10/2011 | el Kaliouby et al. | |
| 2012/0109452 A1 | 5/2012 | Autran et al. | |
| 2012/0278904 A1* | 11/2012 | Perez | G06F 21/10 726/31 |
| 2012/0324491 A1 | 12/2012 | Bathiche et al. | |
| 2013/0023337 A1 | 1/2013 | Bowers et al. | |
| 2013/0116587 A1 | 5/2013 | Sornmo et al. | |
| 2013/0197409 A1 | 8/2013 | Baxter et al. | |
| 2013/0204455 A1 | 8/2013 | Chia et al. | |
| 2014/0171752 A1 | 6/2014 | Park et al. | |
| 2014/0172910 A1 | 6/2014 | Jung et al. | |
| 2014/0218187 A1* | 8/2014 | Chun | G08B 21/06 340/439 |
| 2014/0309806 A1* | 10/2014 | Ricci | B60R 25/1004 701/1 |
| 2014/0309870 A1* | 10/2014 | Ricci | B60W 50/14 701/36 |
| 2015/0258995 A1 | 9/2015 | Essers et al. | |
| 2016/0001781 A1* | 1/2016 | Fung | B60R 25/25 701/36 |
| 2016/0104486 A1 | 4/2016 | Penilla et al. | |
| 2017/0003784 A1 | 1/2017 | Garg et al. | |
| 2017/0021282 A1* | 1/2017 | Comploi | A63G 25/00 |
| 2017/0337438 A1* | 11/2017 | el Kaliouby, Jr. | A61B 5/0077 |
| 2018/0143635 A1* | 5/2018 | Zijderveld | B60W 40/08 |
| 2018/0157923 A1* | 6/2018 | el Kaliouby, Jr. | G06K 9/6218 |
| 2019/0073547 A1* | 3/2019 | el Kaliouby | A61B 5/18 |
| 2019/0110103 A1* | 4/2019 | el Kaliouby | G08G 1/0112 |
| 2019/0133510 A1* | 5/2019 | el Kaliouby | G06N 3/084 |
| 2019/0152492 A1* | 5/2019 | el Kaliouby | G06K 9/627 |
| 2019/0162549 A1* | 5/2019 | Fouad | G06K 9/00315 |
| 2019/0197330 A1* | 6/2019 | Mahmoud | A61B 5/7257 |
| 2019/0283762 A1* | 9/2019 | el Kaliouby | B60W 40/08 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming HE, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

\* cited by examiner

SPORADIC COLLECTION OF AFFECT DATA WITHIN A VEHICLE

RELATED APPLICATIONS

This application a continuation-in-part of U.S. patent application "Sporadic Collection with Mobile Affect Data" Ser. No. 14/961,279, filed Dec. 7, 2015, which claims the benefit of U.S. provisional patent applications "Viewership Analysis Based on Facial Evaluation" Ser. No. 62/128,974, filed Mar. 5, 2015, "Mental State Event Signature Usage" Ser. No. 62/217,872, filed Sep. 12, 2015, and "Image Analysis In Support of Robotic Manipulation" Ser. No. 62/222,518, filed Sep. 23, 2015. This application is also a continuation-in-part of U.S. patent application "Sporadic Collection of Mobile Affect Data" Ser. No. 14/064,136, filed Oct. 26, 2013, which claims the benefit of U.S. provisional patent applications "Sporadic Collection of Mobile Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013. This application is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. This application is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based on Facial Evaluation" Ser. No. 62/128,974, filed Mar. 5, 2015; the application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011; the application is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014 and is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

This application is also a continuation-in-part of U.S. patent application "Vehicle Manipulation Using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017. The patent application "Vehicle Manipulation Using Occupant Image Analysis" Ser. No. 15/875,644, filed Jan. 19, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016. The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015. The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The foregoing applications are each hereby incorporated by reference in their entirety.

FIELD OF ART

This application relates generally to analysis of mental states and more particularly to sporadic collection of affect data within a vehicle.

BACKGROUND

Users spend seemingly endless amounts of time interacting with computers, smartphones, tablets, and all manner of electronic devices. These interactions include copious amounts of media consumption, web surfing, and online commerce, to name only a few. This interaction may be for many different reasons such as education, entertainment, social media interaction, document creation, and gaming, to name a few. The human-computer interaction can take the form of a person performing a task using a software-based tool running on a computer. Examples include filling out a tax form, creating a document, editing a video, and/or doing one or more of the numerous other activities performable by a modern computer. The person can find the execution of certain activities interesting or even exciting, and may be surprised at how easy it is to perform the activity. The person may become excited, happy, or content as he or she performs such an interesting or exciting activity. On the other hand, the person can find some activities difficult to perform, and may become frustrated or even angry with the computer or software tool. In some cases, users are surveyed in an attempt to determine where a computer or computer program may be functioning well, and where it may need improvement. However, such survey results are often unreliable since the surveys are often completed well after the activity was performed. Further, survey participation rates may be low, and people may not provide accurate and honest answers to the survey.

For other human-computer interaction, the person is using a software tool to accomplish a task, but instead may be consuming computer-accessed content or media such as news, pictures, music, or video. Currently, while or after consuming computer-driven content, viewers may self-rate the media to communicate personal preferences. In some cases, viewers may enter a specific number of stars corresponding to a level of like or dislike, while in other cases, users may be asked to answer a list of questions. While this system of evaluation is a helpful metric to evaluate media and other products or services, such evaluation may be tedious and challenging. Thus, in many cases, this type of subjective evaluation is neither a reliable nor practical way to evaluate personal response to media. Recommendations based on such a system of star rating or other self-reporting are imprecise, subjective, unreliable, and are further limited by sample size: often, only a small number of viewers actually rate the media they have consumed.

SUMMARY

A user frequently interacts with computers and other personal electronic devices such as smartphones, personal digital assistants (PDAs), tablets, and wearable devices. The interactions with the devices can entail myriad tasks or activities. Further, the user can interact with these devices while within a vehicle. Manifestations of the user-device interactions can include mental states, cognitive states, emotional states, moods, and so on. A given mental state experienced by a user can present in a variety of ways including facial expressions, physiological activity, muscle movements (voluntary and involuntary), or other externally detectable manifestations. A camera, microphone, or a variety of other monitoring components can be used to collect one or more of the externally detectable manifestations of the user's mental state. Particularly while the user is an occupant within a vehicle, the collecting can occur on an intermittent basis. Environmental, timing, traffic, or other conditions can occur where the monitoring device or devices cannot continuously detect the external manifestation.

Techniques are disclosed for sporadic collection of affect data within a vehicle. Mental state data of a vehicle occupant within a vehicle is collected on an intermittent basis. The mental state data includes facial image data and the facial image data is collected intermittently across a plurality of devices within the vehicle. The in-vehicle devices can include cameras or sensors. The mental state data further includes audio information. The audio information can be collected using a microphone, transducer, or other audio capture component. Processors are used to interpolate mental state data in between the collecting which is intermittent. The interpolating can be based on techniques including linear interpolation, polynomial interpolation, and the like. The collection techniques further include imputing additional mental state data where the mental state data is missing. Mental state data collected from other occupants of the vehicle can be used to fill in mental state data missing from the vehicle occupant. Analysis of the mental state data on the vehicle occupant is obtained, where the analysis of the mental state data includes analyzing the facial image data. The analysis can be performed by a processor within the vehicle, a personal electronic device associated with the vehicle occupant, a remote computer such as a server, a web service, and the like. The analysis of the mental state data can be augmented with the audio information. An output is rendered based on the analysis of the mental state data. The rendering can include communication by a virtual assistant. The assistant can communicate inside the vehicle with the occupant via audio. The virtual assistant can include an avatar display. The rendering includes communication with a navigation component of the vehicle. The rendering can include manipulating the vehicle, where the vehicle can include an autonomous vehicle or a semi-autonomous vehicle. The manipulating can include operating the vehicle in autonomous mode. The rendering can be used to communicate the output to a second vehicle, where the second vehicle is used by the occupant. The technique further includes translating the mental state data into an emoji for representation of the occupant. The emoji can be presented on a display within the vehicle, on a display coupled to a personal electronic device, on a social media platform, and so on.

In embodiments, a computer-implemented method for mental state analysis comprises: collecting mental state data of a vehicle occupant within a vehicle on an intermittent basis wherein the mental state data includes facial image data and the facial image data is collected intermittently across a plurality of devices within the vehicle; interpolating, using one or more processors, mental state data in between the collecting which is intermittent; obtaining analysis of the mental state data on the vehicle occupant, wherein the analysis of the mental state data includes analyzing the facial image data; and rendering an output based on the analysis of the mental state data. In some embodiments, a computer program product is embodied in a non-transitory computer readable medium for mental state analysis, the computer program product comprising code which causes one or more processors to perform operations of: collecting mental state data of a vehicle occupant within a vehicle on an intermittent basis wherein the mental state data includes facial image data and the facial image data is collected intermittently across a plurality of devices within the vehicle; interpolating, using one or more processors, mental state data in between the collecting which is intermittent; obtaining analysis of the mental state data on the vehicle occupant, wherein the analysis of the mental state data includes analyzing the facial image data; and rendering an output based on the analysis of the mental state data.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
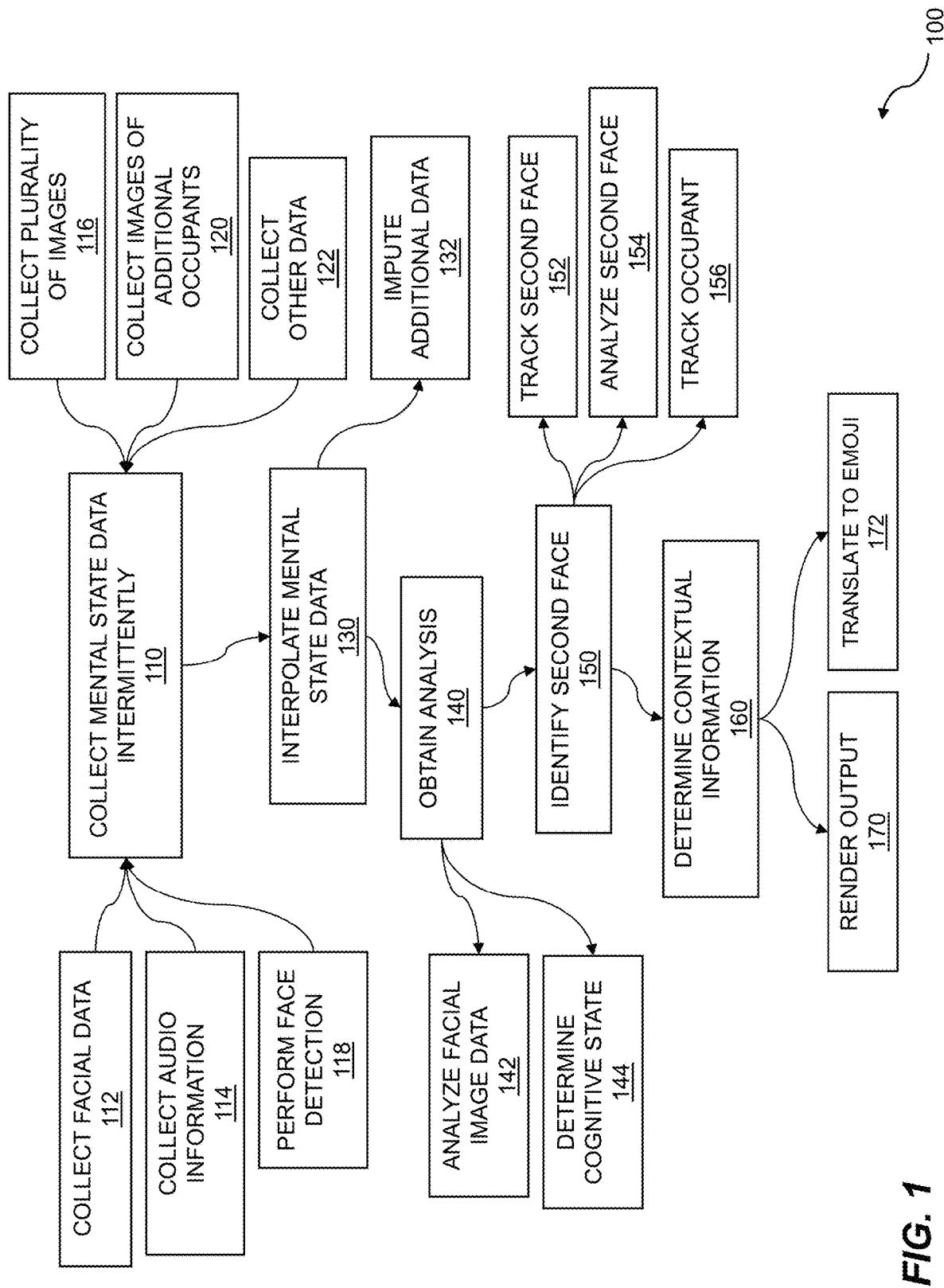
FIG. 1 is a flow diagram for sporadic collection within a vehicle.

A vehicle occupant can experience a variety of mental, cognitive, or emotional states. As the occupant travels in and interacts with the vehicle, the occupant's mental state can provide valuable insight into the nature of the human-vehicle interaction. The occupant experiences events and stimuli within the vehicle such as temperature, sound, vehicle settings, and so on. The occupant also experiences external events and stimuli such as road conditions, interactions with other vehicle operators, etc. The vehicle occupant can experience such wide ranging mental states as drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Gaining insight into an occupant's mental state as she or he interacts with the vehicle may be valuable for a variety of reasons, such as determining which aspects of a vehicle work well and which aspects require improvement.

While within the vehicle, the vehicle occupant can exhibit physical manifestations of her or his one or more mental states. The physical manifestations can include, facial expressions, physiological reactions, and voluntary or involuntary movements. One or more cameras or microphones can be used to collect mental state data on an intermittent basis from the vehicle occupant. The intermittent mental state data can be interpolated to fill in gaps in the collected mental state data. Further, additional mental state data can be imputed. The imputing is based on using mental state data collected from other individuals associated with the vehicle occupant to fill in data missing from the vehicle occupant. Depending on the vehicle occupant and/or the mental state data collection component, continuous capture of the manifestations of mental states may not be possible. For example, if the vehicle occupant looks away from the camera, it may not be possible to capture an image of their face until they look back at the camera. As a further example, a skin resistance sensor embedded in an armrest of the vehicle occupant's armrest can only measure a galvanic skin response if the user's arm is resting on the armrest. In other cases, continuous capture the data from a sensor may be possible, but may not be practical or desirable due to captured data volume, or the relative slowness of measurable change of the manifestation of a particular mental state.

Data relating to manifestations of a mental state that can be collected by a camera, microphone, or sensor, can be collected on an intermittent basis. The intermittent basis for the capture of mental state data such as affect data can be sporadic, opportunistic, periodic, random, or on any other non-continuous basis. Data from the camera, microphone, or sensors can be captured based on the ability of the sensor to capture valid data. The validity of the data can be based on usefulness of the captured data, a data capture schedule or opportunity, or indications from other sensors. In a usage example, an image from a camera might only be saved for further analysis if some form of preprocessing detects that a face is visible within the image. Similarly, video data of a vehicle occupant's body (used for movement analysis) may be taken only when triggered by a change in heart rate detected by a heart rate monitor, or audio information might only be stored when speech or non-speech vocalizations are detected. A wide variety of techniques may be used to intermittently collect, capture, and/or store data related to a mental state of the vehicle occupant. Processors can be used to interpolate mental state data in between the collecting which is intermittent. The processors can be used to impute missing data associated with the vehicle occupant by collecting mental state data from other occupants of the vehicle and using that collected data to fill in the missing data from the vehicle occupant. Analysis of the mental state data can be obtained, where the analysis includes analysis of the facial image data. The analysis of the mental state data can further include analysis of the collected audio information. The analysis can be performed locally on a processor within the vehicle, on a personal electronic device within the vehicle, on a processor remote from the vehicle such as a server or cloud-based analysis service, and so on. An output can be rendered, where the rendering can include using a virtual assistant which can communicate with the occupant via audio. The virtual assistance can further include an avatar display. The mental state data can be translated into an emoji for representation of the occupant. The emoji, can be rendered on a display within the vehicle or a display coupled to a personal electronic device, can be posted on a social media site, and so on.

FIG. 1 is a flow diagram for sporadic collection within a vehicle. The sporadic collection includes sporadic collection of affect data within a vehicle. The flow 100 includes collecting mental state data of a vehicle occupant within a vehicle on an intermittent basis 110. Any non-continuous collection of mental state data can be considered collection on an intermittent basis. In some embodiments, the intermittent basis can be opportunistic, where the intermittent basis can be either sporadic or occasional. The intermittent basis can include the capture of images at time-random intervals, at times when the individual takes certain actions, at times when the user happens to look in the direction of a camera, and so on. The mental state data includes facial image data 112 and the facial image data is collected intermittently across a plurality of devices within the vehicle. The collecting mental state data can be based on image analysis of the facial data. The facial data can be obtained from a series of images of the individual where the series of images can include a series of still images, frames extracted from a video, etc. In other embodiments, the intermittent basis can be periodic, and can occur on a regular schedule. For example, one or more images of the user can be collected once every 30 seconds. In some embodiments, the intermittent basis can be a combination of occasional and periodic collection. For example, the collecting can include collecting mental state data once every minute plus additional data collection each time the user performs some act. The act that the user can perform can include clicking a mouse button, hitting a particular key such as the 'Enter' key on a computer keyboard, touching or swiping a screen on a handheld device, tilting a handheld device, and so on. The collecting can be accomplished for one or more types of mental state data. In further embodiments, the facial image data can be obtained from a series of images of the occupant.

In embodiments, the collecting mental state data further includes collecting audio information 114 on the vehicle occupant. The audio information can be collected from a plurality of microphones, transducers, or other audio capture component. In embodiments, the audio information is intermittent. The sources of the audio information can include one or more vehicle occupants, in-vehicle sources, outside vehicle sources, etc. In embodiments, the audio information can include speech. The speech can include single words, general phrases, key phrases, and the like. In embodiments, the audio information can include non-speech vocalizations. The non-speech vocalizations can be generated by one or more occupants of the vehicle. The occupant can be the driver of the vehicle, a passenger in the vehicle, and the like. In embodiments, the non-speech vocalizations include grunts, yelps, squeals, snoring, sighs, laughter, filled pauses, unfilled pauses, or yawns.

In the flow 100, the collecting mental state data includes collecting a plurality of images 116. The plurality of images can be collected from a single camera or image capture device or from a plurality of cameras or image capture devices. The images can be of the vehicle occupant or a plurality of vehicle occupants, where the vehicle occupants can be within the same vehicle as the vehicle occupant or distributed among multiple vehicles. In embodiments, the plurality of images can include near-infrared images. Other electromagnetic wavelengths may also be used for mental state data collection. The flow 100 further includes performing face detection 118 to determine when the occupant is looking in the direction of the camera. One or more images can be captured when the occupant is looking in the direction of a given camera, or not captured when the occupant is looking away from the camera. Various techniques can be used for performing face detection. In embodiments, the face detection can be based on image classifiers. One or more classifiers can be used by a neural network or other network suitable to machine learning or deep learning, for identifying a face in an image.

Many different types of mental state data can be collected. For example, the mental state data can include one or more of a group including physiological data, facial data, accelerometer data, and so on. Any appropriate sensors can be used for the collection of mental state data. The collecting of the mental state data can be accomplished using a variety of different sensors that can be chosen depending on the type of mental state data being collected. In at least one embodiment, a camera coupled to a computer or other portable or handheld electronic device can be used to capture mental state data, where the mental state data can include facial data such as facial expressions. Facial expressions that can be used to infer mental state data can include one or more of smiles, laughter, smirks, grimaces, etc. The mental state data also can include one or more of head position, up/down head motion, side-to-side head motion, tilting head motion, body leaning motion, gaze direction, and so on. The mental state data can be captured using a camera, an accelerometer, eye-tracking glasses, or other types of sensors. In some embodiments, the collecting of mental state data can be accomplished with a mobile device, a handheld device, a personal electronic device, etc.

The flow 100 further includes obtaining additional images of one or more additional occupants of the vehicle 120. The additional occupants can include the driver of the vehicle, one or more passengers within the vehicle, and so on. The additional images can be collected sporadically, intermittently, etc. The additional images can be analyzed to determine one or more additional cognitive states or mental states. The cognitive states or mental states can be similar to those of the vehicle occupant or different from those of the vehicle occupant. The flow 100 includes collecting other mental state data from the occupant on a continuous basis 122. The other mental state data collected on a continuous basis can include image data, physiological data, etc. In embodiments, the other mental state data can include audio data. As discussed throughout, the audio data can include speech, non-speech vocalizations, vehicle interior sounds, vehicle exterior sounds, and the like. In embodiments, the mental state data of an occupant collected on an intermittent basis includes audio voice data.

The flow 100 includes interpolating, using one or more processors, mental state data 130 in between the collecting which is intermittent. The interpolating can be based on forming or calculating data between known data, where the known data can include mental state data. The interpolating can include calculating or predicting a mental state that may occur between mental states that can be collected from intermittent facial image data, voice data, etc. The interpolating can be accomplished based on various techniques including piecewise constant interpolation, linear interpolation, polynomial interpolation, and so on. The flow 100 further includes imputing additional mental state data 132 where the mental state data is missing. The mental state data can be missing due to missing image data or audio data, where the missing data can result from a vehicle occupant looking away, not being visible to a camera or image capture device, not within range of a microphone, etc. The imputation can include replacing missing data with substituted values. The substituted values can be found within the dataset (e.g. hot-decking), found within a different dataset (cold-decking), and so on. The imputation can be used to reduce the effect of a bias that can result from calculations affected by the missing data. In embodiments, the imputing can be based on mental state data collected from other individuals associated with the vehicle occupant.

The flow 100 includes obtaining analysis of the mental state data on the vehicle occupant 140. The analysis can be performed using one or more processors. The one or more processors can be located locally or remotely. For example, the processors for obtaining analysis can be collocated with image capture, included in a user device, and so on. In embodiments, the analysis of the mental state data includes analyzing the facial image data 142. The analyzing the facial image data can include determining whether a face is present within an image. The determining whether a face is present within an image can be based on using one or more image classifiers. The analyzing the facial image data can include associating the face with the vehicle occupant. Further embodiments include analyzing the mental state data to determine a cognitive state 144. The cognitive state can be associated with the vehicle occupant. The vehicle occupant can experience more than one cognitive state. Additional images of one or more additional occupants of the vehicle can be obtained. The additional images can be analyzed to determine one or more additional cognitive states. In embodiments, the cognitive state of the vehicle occupant and/or the one or more additional occupants can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

The flow 100 includes identifying a second face 150 from a second individual within the series of images. When additional individuals can be identified within a series of images, a third face, a fourth face, and so on, can be identified within the series of images. The second face, the third face, and so on, can be identified with the one or more images using one or more image classifiers. The identifying the faces can be used for a variety of purposes further to identifying. Further embodiments include tracking the second face 152 within the series of images. The tracking can include determining whether the second face is visible within a series of images; is translated, rotated, or scaled between images; etc. The tracking can include tracking of faces in addition to the second face. Embodiments include analyzing the second face for mental state data 154. Discussed throughout, the analysis of the mental state data can be used to determine one or more mental states such as drowsiness, fatigue, cognitive overload, satisfaction, etc. Further embodiments include tracking a face for the occupant 156 within the series of images. The tracking the face for the occupant can include determining a direction of gaze of the occupant. The tracking of first and the second face can include scaling, rotation, translation, leaving, reappearing, and so on.

The flow 100 includes determining contextual information 160. The contextual information can be based on sensor data or other types of data such as the application being used on a computer or personal electronic device, the time of day, or any other type of contextual information. The contextual information can be based on one or more of skin temperature or accelerometer data. In embodiments, other physiological information can be included in contextual information, where the physiological data can include one or more of electrodermal activity, heart rate, heart rate variability, skin temperature, or respiration, and so on. The contextual information can be based on one or more of a photograph, an email, a text message, a phone log, or GPS information. The flow 100 includes rendering an output 170 based on the analysis of the mental state data. As discussed throughout, the rendering can include communication by a virtual assistant, where the virtual assistant can communicate within the vehicle. The virtual assistant can communicate with the occupant of the vehicle using a variety of techniques. In embodiments, the virtual assistant communicates with the occupant via audio, where the audio can include speech, alarms, tones, signals, music, etc. The virtual assistant can interact with the vehicle occupant by communicating using speech. In other embodiments, the virtual assistant can include an avatar display. The avatar display can be rendered on a heads up display, a display mounted within the vehicle, a display coupled to a personal electronic device associated with the vehicle occupant, etc. The flow 100 further includes translating the mental state data into an emoji 172 for representation of the occupant. The emoji can be represented to the occupant on an in-vehicle display, a display coupled to the personal electronic device, and so on. More than one emoji can be translated when the vehicle occupant is experiencing more than one mental state. An emoji, pictograph, emoticon, etc., can represent facial expressions, places, animals, food, cultural items, and so on. An emoji can be shared by the individual with others including friends, family, and so on, through social media, email messages, text (SMS) messages, and so on. The emoji can be automatically selected based on the mental state data, chosen by the individual, chosen by others to represent one or more mental states of the individual, and so on. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors. Various embodiments of the flow 100, or portions thereof, can be included on a semiconductor chip and implemented in special purpose logic, programmable logic, and so on.

Figure 2:
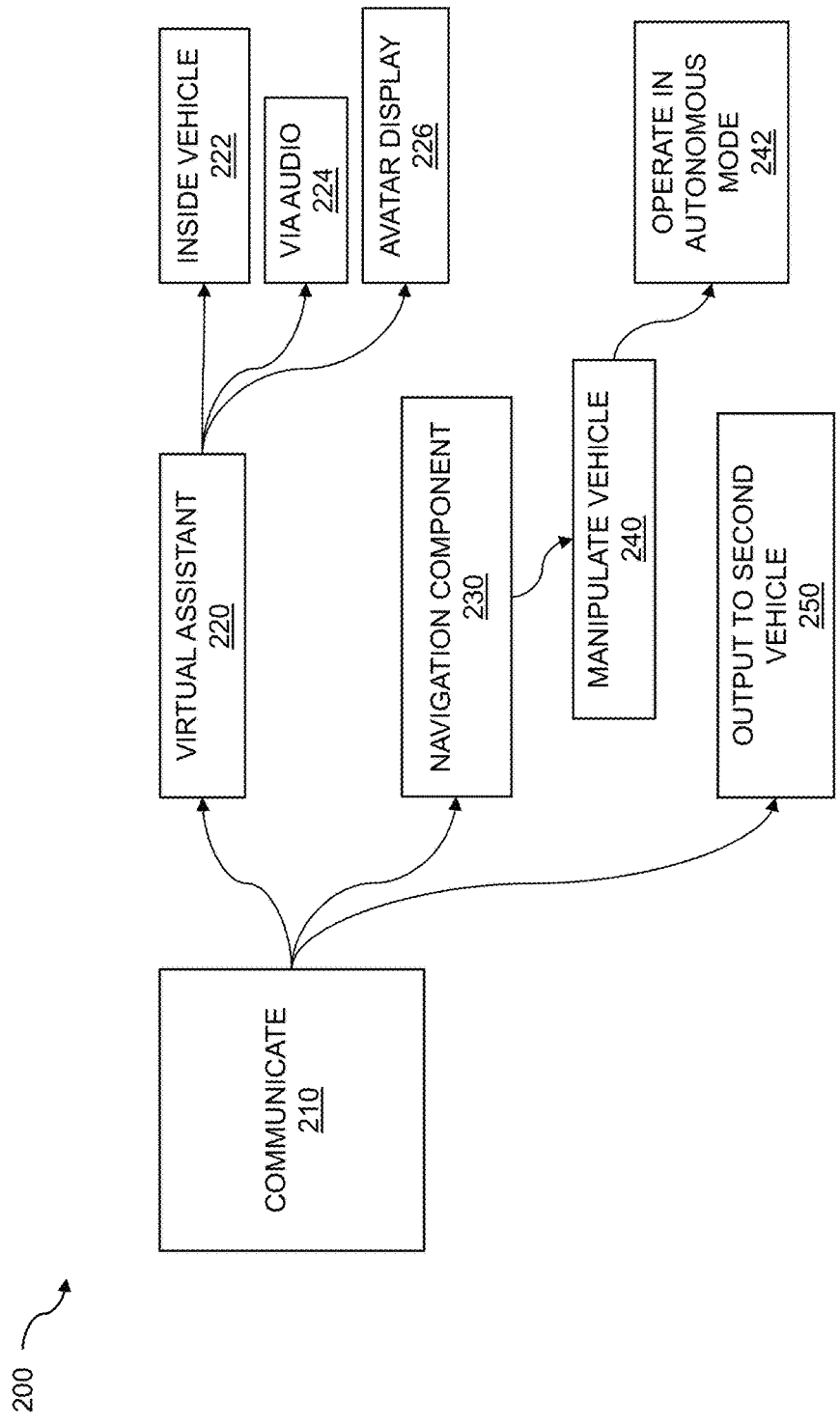
FIG. 2 is a flow diagram for communicating results of mental state analysis for a vehicle occupant.

FIG. 2 is a flow diagram for communicating results of mental state analysis for a vehicle occupant. An output can be rendered based on analysis of the collected mental state data, facial image data, audio information, and so on. The output or other information can be communicated to a vehicle, to a vehicle occupant, etc. The communicating can be based on mental state analysis, where the mental state analysis includes sporadic collection of affect data within a vehicle. Mental state data of a vehicle occupant is collected within a vehicle on an intermittent basis. The mental state data includes facial image data which is collected intermittently across a plurality of devices within the vehicle. The mental state data can further include audio information. Processors are used to interpolate mental state data in between the collecting which is intermittent. Additional mental state data can be imputed where the mental state data is missing. The imputing is based on mental state data collected from other individual associated with the vehicle occupant. Analysis of the mental state data on the vehicle occupant is obtained, where the analysis of the mental state data includes analyzing the facial image data. An output is rendered based on the analysis of the mental state data. The rendering can include manipulating a vehicle such as an autonomous vehicle. The rendering can include communication by a virtual assistant, where the virtual assistant can communicate via audio or an avatar display. The mental state data can be translated into an emoji for representation of the occupant.

The flow 200 includes communicating 210. The communicating can include displaying data such as sporadically or continuously collected mental state data; outputting a rendering; sending command or control information; and so on. The communicating can be accomplished using wired techniques such as the Internet or other computer network; wireless techniques such as 802.11, Bluetooth™, Zigbee, or near-field communication (NFC); or hybrid wired/wireless techniques. The communicating can occur between a server, remote computer, or the like, and a vehicle, a personal electronic device within the vehicle, etc. The communicating can be based on a rendering. In the flow 200, the rendering includes communication by a virtual assistant 220. The virtual assistant can include an agent such as a software or code-based agent that can perform tasks in response to spoken instructions from a vehicle occupant. The virtual assistant can speak, display, or otherwise convey information such as travel route suggestions, recommended sound tracks, weather alerts, and the like to the vehicle occupant. In embodiments, the virtual assistant can communicate inside the vehicle 222. The virtual assistant can communicate based on sounds, tones, messages, and so on. The communication inside the vehicle by the virtual assistant can include playing a message on a sound system, flashing a message on a personal electronic device associated with the vehicle occupant, etc. In the flow 200, the virtual assistant communicates with the occupant via audio 224. The audio communication to the occupant can include a query, a message, route recommendations, a play list, etc. The audio communication to the occupant can be delivered through the vehicle sound system, through the occupant's personal electronic device, and the like. In embodiments, the vehicle occupant is a driver of the vehicle. In the flow 200, the virtual assistant includes an avatar display 226. The avatar display can include an emoji, an animated emoji, a cartoon or animation, a GIF, a still image, and so on. The avatar can be displayed on a heads up display, an in-vehicle display, a personal electronic device associated with the occupant, etc.

In the flow 200, the rendering includes communicating with a navigation component of the vehicle 230. The navigation component of the vehicle can include a mapping component such as a GPS or a mapping app on a personal electronic device, a controller component such as the controller of an autonomous or semi-autonomous vehicle, and so on. In embodiments, the rendering includes manipulating the vehicle 240. The manipulating the vehicle can include setting mirrors or seats, choosing vehicle interior climate settings, starting a preferred playlist, etc. The manipulating the vehicle can include turning on headlights, setting windshield wiper speed, and the like. In embodiments, the manipulating the vehicle includes operating the vehicle in autonomous mode 242. The vehicle can be operated in autonomous mode, semiautonomous mode, etc., as a convenience to the vehicle occupant. The vehicle can be operated in autonomous to permit access to the vehicle, to lockout the vehicle to an impaired driver, or based on other safety objectives. The vehicle can be operated in a semi-autonomous mode based on the manipulating. In the flow 200, the rendering includes communicating the output to a second vehicle 250. Results of mental state analysis can be used across multiple ride sessions. Those multiple ride sessions can be within the same vehicle or across a plurality of vehicles. The communicating the output to a second vehicle can include sending an alert to an occupant of the second vehicle, manipulating the second vehicle to avoid a dangerous situation, etc. In embodiments, the second vehicle can be used by the occupant. The second vehicle can be owned by the occupant, shared by the occupant, operated by the occupant, and so on. The second vehicle can be another vehicle in a fleet of vehicles. The second vehicle can be similar to a first vehicle, such as a similar model of vehicle, or can be dissimilar to the first vehicle. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors.

Figure 3:
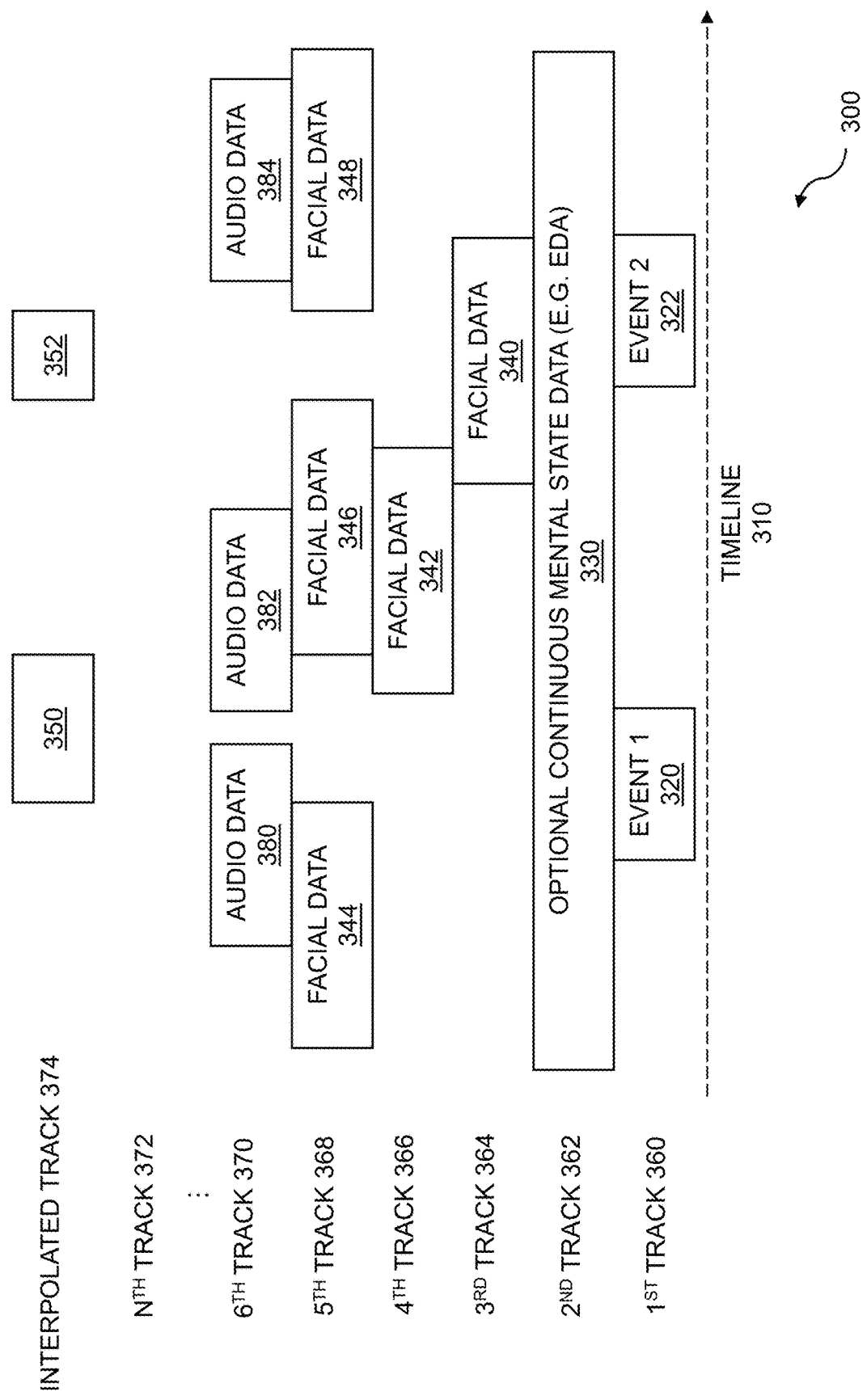
FIG. 3 is a timeline with information tracks relating to mental states.

FIG. 3 is a timeline with information tracks relating to mental states. The timeline can illustrate relative times of sporadic collection of affect data within a vehicle. Mental state data of a vehicle occupant is collected within a vehicle on an intermittent basis where the mental state data includes facial image data and the facial image data is collected intermittently across a plurality of devices within the vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include communicating with an automated assistant using audio or an avatar display. The rendering can include communicating with a vehicle navigation component for manipulating the vehicle. The rendering can include communicating the output to a second vehicle where the second vehicle is used by the occupant.

A timeline 310 can show information tracks 300, where the information that can be represented by the tracks can be collected on an intermittent basis. A first track 360 shows events that may be related to the individual's use of a computer or other device. A first event 320 may indicate an action that the individual took (such as launching an application); an action initiated by the computer (such as the presentation of a dialog box); an external event (such as a new global positioning system (GPS) coordinate); or receiving an e-mail message, a phone call, a text message, or any other type of event. In some embodiments, a photograph may be used to document an event or simply to save contextual information in the first track 360. A second event 322 may indicate another action or event. Such events can be used to provide contextual information and can also include such things as copies of email messages, text messages, phone logs, file names, or other information that may be useful to determine or understand contextual information that can relate to actions of a user. In embodiments, contextual information can be based on one or more of a photograph, an email, a text message, a phone log, or GPS information.

A second track 362 can include continuously collected mental state data such as electrodermal activity data 330. In embodiments, a track can include intermittently collected mental state data. The intermittently collected data can be collected when an individual is present in an image and not collected when the individual is absent from the image, for example. The intermittently collected data can include facial data where the facial data is collected intermittently when the individual can be looking in a direction of a camera. The camera can be a still camera, a video camera, a camera coupled to a mobile device, etc. The intermittent data collection can occur across multiple devices. For example, when the individual is facing a smartphone, then the facial data can be collected from the camera coupled to the smartphone; when the individual is facing a laptop, then the facial data can be collected from the camera coupled to the laptop, and so on. Any number of devices can be used to collect facial data intermittently over time.

A third track 364 can include facial data 340, which can be a type of mental state data that is collected on an intermittent basis by a first camera, such as a room camera or vehicle camera, (although in some embodiments, the facial data can be collected continuously). The facial data can be collected intermittently when the individual is looking toward a camera. The facial data 340 can include one or more still photographs, videos, or abstracted facial expressions which can be collected when the user looks in the direction of the camera. A fourth track 366 can include facial data 342 that can be collected on an intermittent or continuous basis by a second camera, such as the mobile phone camera. The facial data 342 can include one or more still photographs, videos, or abstracted facial expressions which can be collected when the user looks in the direction of that camera. A fifth track 368 can include facial data that is collected from a third camera, such as the webcam. In the example shown, the fifth track 368 includes facial data 344, additional facial data 346, and yet further facial data 348 which can be any type of facial data including data that can be used for determining mental state information. Any number of samples of facial data can be collected in any track. The mental state data from the various tracks can be collected simultaneously, collected on one track exclusive of other tracks, collected where mental state data overlaps between the tracks, and so on. When mental state data from multiple tracks overlaps, one track's data can take precedence over the others or the data from the multiple tracks can be combined.

A sixth track 370 can include audio information, where the audio information can be a type of mental state data that is collected on an intermittent basis by one or more microphones. A first microphone can be a microphone within the vehicle, a microphone coupled to a portable electronic device such as a smartphone, tablet, or PDA, a microphone outside the vehicle, and the like. The audio information can include speech, where the speech can be generated by the vehicle occupant, a driver of the vehicle, a passenger within the vehicle, etc. The audio information can include non-speech vocalizations, where the non-speech vocalizations can emanate from one or more vehicle occupants. In embodiments, the non-speech vocalizations can include grunts, yelps, squeals, snoring, sighs, laughter, filled pauses, unfilled pauses, or yawns. The audio data collected on an intermittent basis can include audio data 380, additional audio data 382, further audio data 384, and the like. The audio data may be collected while a vehicle occupant is facing in the direction of a microphone or other audio collected component.

Additional tracks, through the $n^{th}$ track 372, of mental state data of any type may be collected. The additional tracks 372 can be collected on a continuous or on an intermittent basis. The tracks can include mental state data including audio voice data. The mental state data of an individual can include audio voice data captured on an intermittent basis. The intermittent basis for mental state data can be either occasional or periodic. The intermittent basis can occur when the individual is facing a camera. The analysis can further include interpolating mental state analysis in between the collecting which is intermittent; collecting other mental state data, including electrodermal activity data, from the individual on a continuous basis; imputing additional mental state data where the mental state data is missing; filtering out faces of one or more other people to determine when an individual is looking in a direction of a camera; determining contextual information based on accelerometer data; and rendering an output based on the analysis of the mental state data. The intermittent collection of mental state data can be obtained with multiple devices where the data collection can take place when the individual is looking in the direction of at least one of the plurality of image collection devices.

One or more interpolated tracks 374 may be included and may be associated with mental state data that is collected on an intermittent basis, such as the facial data of the fifth track 368. Interpolated data 350 and further interpolated data 352 may contain interpolations of the facial data of the fifth track 368 for the time periods where no facial data was collected in that track. Other embodiments interpolate data for periods where no track includes facial data. In further embodiments, analysis includes interpolating mental state analysis when the mental state data collected is intermittent.

The mental state data, such as the continuous mental state data 330, and/or any of the collected facial data 340, 342, 344, 346, and 348, and/or any of the collected audio data 380, 382, and 384 can be tagged. The tags can include metadata related to the mental state data, including, but not limited to, the device that collected the mental state data; the individual from whom the mental state data was collected; the task being performed by the individual; the media being viewed by the individual; and the location, environmental conditions, time, date, or any other contextual information. The tags can be used to locate pertinent mental state data; for example, the tags may be used to retrieve the mental state data from a database. The tags can be included with the mental state data that is sent over the internet to cloud or web-based storage and/or services so that the tags may be used locally on the machine where the mental state data was collected and/or remotely on a remote server or a cloud/web service.

Figure 4:
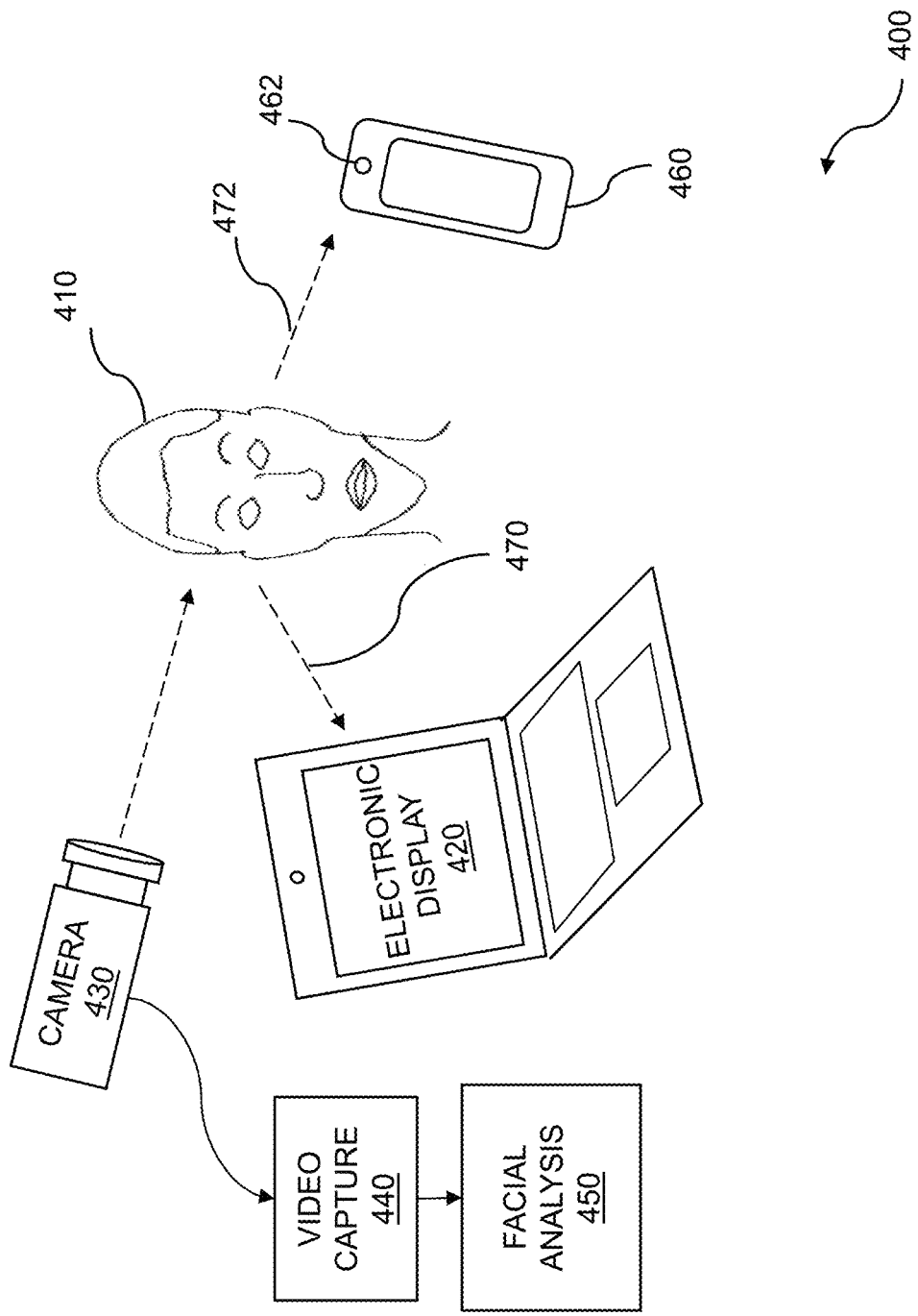
FIG. 4 is a diagram for facial analysis.

FIG. 4 is a diagram for facial analysis 400. Facial analysis can be based on mental state analysis, where the mental state analysis includes sporadic collection of affect data within a vehicle. Mental state data of a vehicle occupant is collected within a vehicle on an intermittent basis. The mental state data includes facial image data and the facial image data is collected intermittently across a plurality of devices within the vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include manipulating a vehicle such as an autonomous vehicle. The rendering can include communication by a virtual assistant, where the virtual assistant can communicate via audio or an avatar display. The mental state data can be translated into an emoji for representation of the occupant.

An individual 410 may view 470 an electronic display 420 while mental state data on the individual 410 may be collected and analyzed. The mental state data can be collected sporadically with mobile affect data. The electronic display 420 may show an output of a computer application that the individual 410 is using, or the electronic display 420 may show a media presentation in a manner which exposes the individual 410 to the media presentation. The media presentation may include one of a group consisting of a movie, a television show, a web series, a webisode, a video, a video clip, an electronic game, an e-book, or an e-magazine. The electronic display 420 may be a part of, or may be driven from, the device collecting the mental state data or, depending on the embodiment, the electronic display may only be loosely coupled to, or may be unrelated to, the device collecting the mental state data. The collecting, in some embodiments, is accomplished with a mobile device 460, such as a cell phone, a tablet computer, or a laptop computer, and the mobile device may include a forward-facing camera 462 which is accessed when the user views 472 the mobile device 460. The facial data may be collected with a camera such as the forward-facing camera 462 of the mobile device 460 and/or by a webcam 430. The facial data may be collected intermittently when the individual 410 is looking in the direction of a camera 462 or 430. The camera may also capture images of the setting. These images may be used in determining contextual information.

The webcam 430 may be used to collect one or more of facial data and physiological data. The facial data may include, in various embodiments, information on facial expressions, action units, head gestures, smiles, smirks, brow furrows, squints, lowered eyebrows, raised eyebrows, or attentiveness. The webcam 430 may capture video, audio, and/or still images of the individual 410. A webcam, as the term is used herein, may include a video camera, still camera, thermal imager, CCD device, phone camera, three-dimensional camera, a depth camera, multiple webcams used to show different views of a person, or any other type of image capture apparatus that may allow data captured to be used in an electronic system. The images of the person 410 from the webcam 430 may be captured by a video capture unit 440. In some embodiments, video may be captured, while in others, one or more still images may be captured. The captured video or still images may be used in facial analysis 450 or for determining gestures, actions, or other movements.

Analysis of facial expressions, gestures, and mental states may be accomplished using the captured images of the person 410. The facial expressions may be used to identify smiles, frowns, and other facial indicators of mental states. The gestures, including head gestures, may indicate interest or curiosity. For example, a head gesture of moving toward the electronic display 420 may indicate increased interest in the media or desire for clarification. Based on the captured images, analysis of physiological data may be performed. Respiration, heart rate, heart rate variability, perspiration, temperature, and other physiological indicators of mental state may be determined by analyzing the images.

Figure 5:
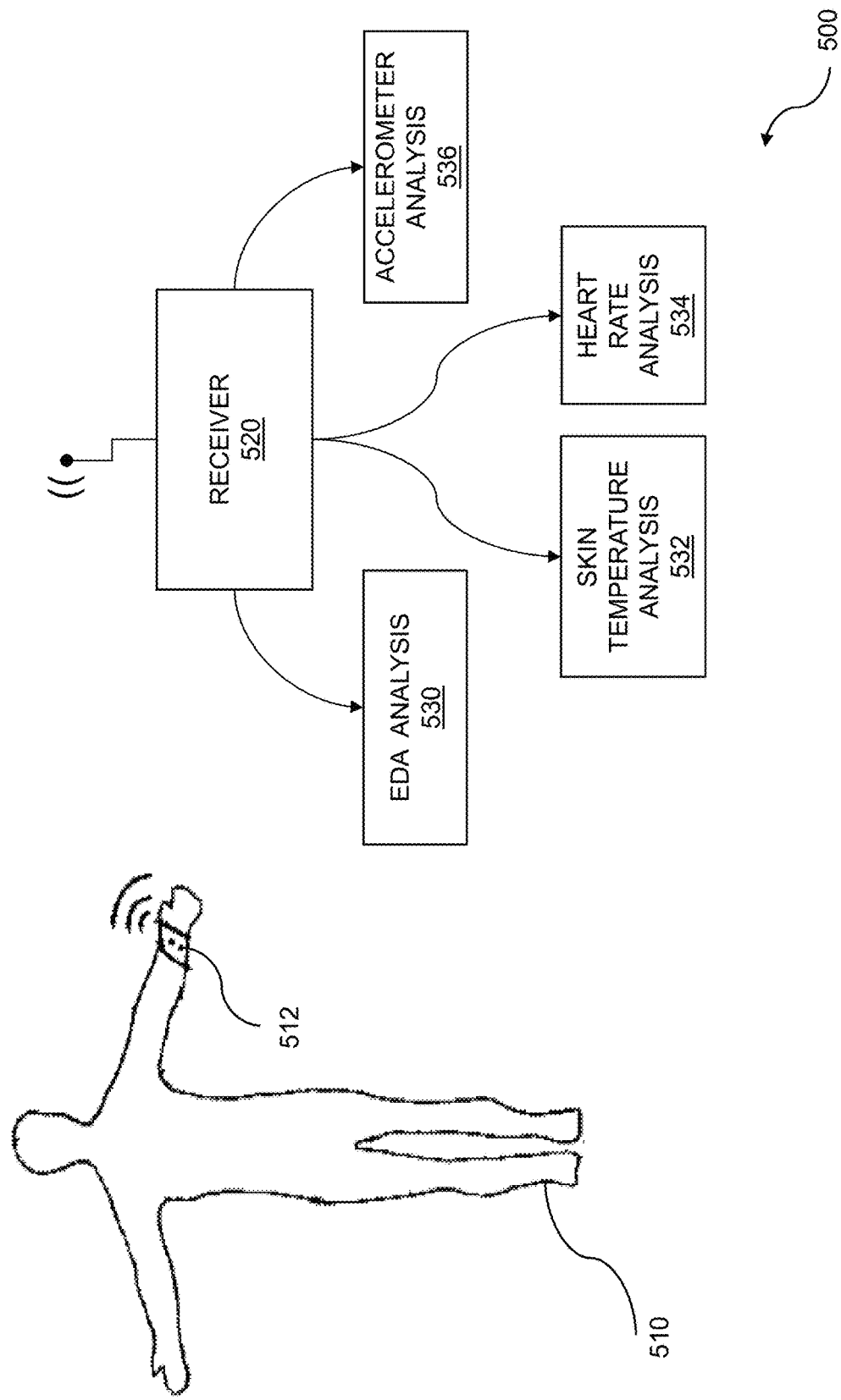
FIG. 5 is diagram for sensor analysis.

FIG. 5 is diagram for sensor analysis. A system 500 may analyze data collected intermittently from a person 510 as she or he interacts with a computer, a mobile device, a handheld device, vehicle controls, screens within a vehicle, and so on. The sensor analysis can be used for sporadic collection of affect data within a vehicle. The person 510 may have a biosensor 512 attached to her or him for the purpose of collecting mental state data. The biosensor 512 may be placed on the wrist, palm, hand, head, or other part of the body. In some embodiments, multiple biosensors may be placed on the body in multiple locations. The biosensor 512 may include detectors for physiological data such as electrodermal activity, skin temperature, accelerometer readings, and the like. Other detectors for physiological data may be included as well, such as heart rate, blood pressure, EKG, EEG, further brain waves, and other physiological detectors. The biosensor 512 may transmit information collected to a receiver 520 using wireless technology such as Wi-Fi, Bluetooth, 802.11, cellular, or other bands. In other embodiments, the biosensor 512 may communicate with the receiver 520 by other methods such as a wired interface or an optical interface. The receiver may provide the data to one or more components in the system 500. In some embodiments, the biosensor 512 may record multiple types of physiological information in memory for later download and analysis. In some embodiments, the download of recorded physiological data may be accomplished through a USB port or other wired or wireless connection.

Mental states may be inferred based on physiological data, such as physiological data from the sensor 512. Mental states may also be inferred based on facial expressions and head gestures observed by a webcam, or a combination of data from the webcam and data from the sensor 512. The mental states may be analyzed based on arousal and valence. Arousal can range from being highly activated—such as when someone is agitated—to being entirely passive—such as when someone is bored. Valence can range from being very positive—such as when someone is happy—to being very negative—such as when someone is angry. Physiological data may include one or more of electrodermal activity (EDA), heart rate, heart rate variability, skin temperature, respiration, accelerometer readings, and other types of analysis of a human being. It will be understood that both here and elsewhere in this document, physiological information can be obtained either by biosensor 512 or by facial observation via the webcam 530. Facial data may include facial actions and head gestures used to infer mental states. Further, the data may include information on hand gestures or body language and body movements such as visible fidgets. In some embodiments, these movements may be captured by cameras, while in other embodiments, these movements may be captured by sensor readings. Facial data may include the tilting the head to the side, leaning forward, smiling, frowning, and many other gestures or expressions.

Electrodermal activity may be collected in some embodiments. It may be collected continuously, every second, four times per second, eight times per second, 32 times per second, or on some other periodic basis. In some embodiments, however, electrodermal activity may be collected on an intermittent basis. The electrodermal activity may be recorded and stored onto a disk, a tape, flash memory, a computer system, or streamed to a server. The electrodermal activity may be analyzed 530 to indicate arousal, excitement, boredom, or other mental states based on observed changes in skin conductance. Skin temperature may be collected and/or recorded on a periodic basis. In turn, the skin temperature may be analyzed 532. Changes in skin temperature may indicate arousal, excitement, boredom, or other mental states. Heart rate may be collected and recorded, and may also be analyzed 534. A high heart rate may indicate excitement, arousal, or other mental states. Accelerometer data may be collected and used to track one, two, or three dimensions of motion. The accelerometer data may be recorded. The accelerometer data may be used to create an actigraph showing an individual's activity level over time. The accelerometer data may be analyzed 536 and may indicate a sleep pattern, a state of high activity, a state of lethargy, or other states. The various data collected by the biosensor 512 may be used along with the facial data captured by the webcam in the analysis of mental states. Contextual information may be based on one or more of skin temperature and/or accelerometer data.

Figure 6:
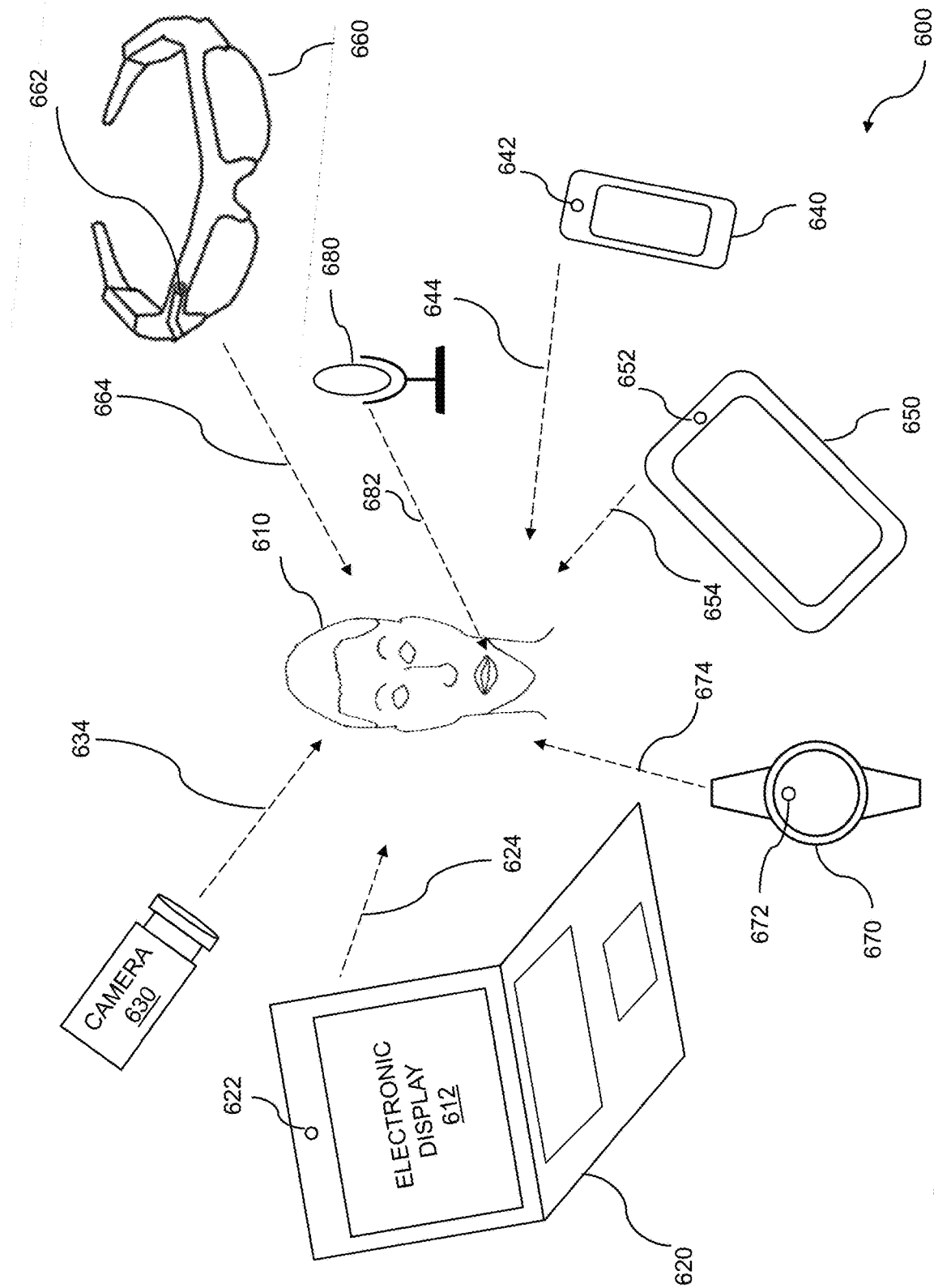
FIG. 6 shows example image and audio collection including multiple devices.

FIG. 6 is a diagram showing image and audio collection including multiple mobile devices. The collection of mental state data from multiple devices can be sporadic, where the collection can take place when a person is looking in the direction of a camera, for example. Image data and audio data can be collected for sporadic collection of affect data within a vehicle. The vehicle itself can be considered a mobile device, or one or more mobile devices within a vehicle can be used for mental state data collection. Mental state data of a vehicle occupant is collected within a vehicle on an intermittent basis. The mental state data includes facial image data which is collected intermittently across a plurality of devices within the vehicle. Processors are used to interpolate mental state data in between the collecting which is intermittent. Analysis is obtained of the mental state data on the vehicle occupant, where the analysis of the mental state data includes analyzing the facial image data. An output is rendered based on the analysis of the mental state data. The rendering can include manipulating a vehicle such as an autonomous vehicle.

While one person is shown, in practice the video data or audio data on any number of people can be obtained. In the diagram 600, the multiple mobile devices can be used separately or in combination to collect video data, audio data, or both video data and audio data on a user 610. While one person is shown, the video data and audio data can be collected on multiple people. A user 610 can be observed as she or he is performing a task, experiencing an event, viewing a media presentation, and so on. The user 610 can be shown one or more media presentations, political presentations, social media, or another form of displayed media. The one or more media presentations can be shown to a plurality of people. The media presentations can be displayed on an electronic display 612 or another display. The data collected on the user 610 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 610 can be analyzed and viewed for a variety of purposes including expression analysis, cognitive state analysis, mental state analysis, emotional state analysis, and so on. The electronic display 612 can be on a laptop computer 620 as shown, a tablet computer 650, a cell phone 640, a television, a mobile monitor, or any other type of electronic device. In one embodiment, video data including expression data is collected on a mobile device such as a cell phone 640, a tablet computer 650, a laptop computer 620, or a watch 670. Similarly, the audio data including speech data and non-speech vocalizations can be collected on one or more of the mobile devices. Thus, the multiple sources can include at least one mobile device, such as a phone 640 or a tablet 650, or a wearable device such as a watch 670 or glasses 660. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 622, a phone camera 642, a tablet camera 652, a wearable camera 662, and a mobile camera 630. A wearable camera can comprise various camera devices, such as a watch camera 672. Sources of audio data 682 can include a microphone 680.

As the user 610 is monitored, the user might move due to the nature of the task, boredom, discomfort, distractions, or for another reason. As the user moves, the camera with a view of the user's face can be changed. Thus, as an example, if the user is looking in a first direction, the line of sight 624 from the webcam 622 is able to observe the user's face, but if the user is looking in a second direction, the line of sight 634 from the mobile camera 630 is able to observe the user's face. Furthermore, in other embodiments, if the user is looking in a third direction, the line of sight 644 from the phone camera 642 is able to observe the user's face, and if the user is looking in a fourth direction, the line of sight 654 from the tablet camera 652 is able to observe the user's face. If the user is looking in a fifth direction, the line of sight 664 from the wearable camera 662, which can be a device such as the glasses 660 shown and can be worn by another user or an observer, is able to observe the user's face. If the user is looking in a sixth direction, the line of sight 674 from the wearable watch-type device 670, with a camera 672 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 610 can also use a wearable device including a camera for gathering contextual information and/or collecting expression data on other users. Because the user 610 can move her or his head, the facial data can be collected intermittently when she or he is looking in a direction of a camera. In some cases, multiple people can be included in the view from one or more cameras, and some embodiments include filtering out faces of one or more other people to determine whether the user 610 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 7:
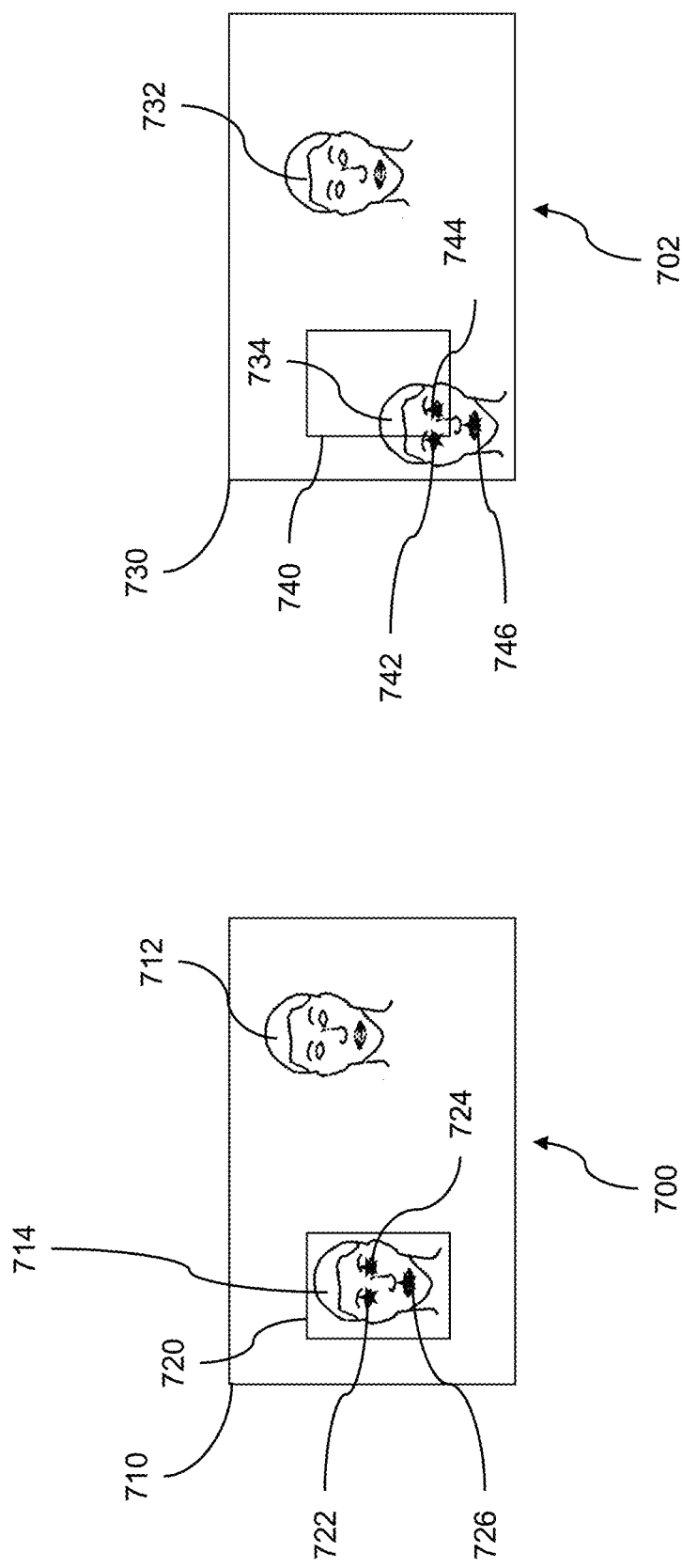
FIG. 7 illustrates feature extraction for multiple faces.

FIG. 7 illustrates feature extraction for multiple faces. Features of a face or a plurality of faces can be extracted from sporadically collected affect data, where the affect data can be collected within a vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include communication by a virtual assistant, where the virtual assistant can communicate inside the vehicle via audio, an avatar display, and so on. The rendering can include communicating with a navigation component of the vehicle, where the communicating includes manipulating the vehicle in an autonomous mode. The mental state data can be translated into an emoji for representation of the occupant.

The feature extraction can be performed by analysis using one or more processors, using one or more a video collection devices, and by using a server, for example. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, for example, by analyzing a known set of data, known as a training set. The training set can include data for which category memberships of the data can be known. The training set can be used as part of a supervised training technique. If a training set is not available, then a clustering technique can be used to group observations into categories. This latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. For example, classification of one or more observations into one or more groups can be based on distributions of the data values, probabilities, and so on. Classifiers can be binary, multiclass, linear and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on.

Classification can be used for biometric identification of one or more people in one or more frames of one or more videos.

Returning to FIG. 7, the detection of the first face, the second face, and so on for any number of faces can include identifying facial landmarks, generating a bounding box, and predicting a bounding box and landmarks for a next frame, where the next frame can be one of a plurality of frames of a video containing faces. In some embodiments, landmark analysis is avoided and instead regions of a face are analyzed. A first video frame 700 includes a boundary 710, a first face 712, and a second face 714. The frame 700 also includes a bounding box 720. Facial landmarks can be generated for the first face 712. Face detection can be performed to initialize a second set of locations for a second set of facial landmarks for a second face within the video. Facial landmarks in the video frame 700 can include the facial landmarks 722, 724, and 726. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. For example, the estimating of a second rough bounding box can include the bounding box 720. Bounding boxes can also be estimated for one or more other faces within the frame 710. The bounding box can be refined, as can one or more facial landmarks. The refining of the second set of locations for the second set of facial landmarks can be based on localized information around the second set of facial landmarks. The bounding box 720 and the facial landmarks 722, 724, and 726 can be used to estimate future locations for the second set of locations for the second set of facial landmarks in a future video frame from the first video frame.

A second video frame 702 is also shown. The second video frame 702 includes a frame boundary 730, a first face 732, and a second face 734. The second frame 702 also includes a bounding box 740 and the facial landmarks 742, 744, and 746. In other embodiments, any number of facial landmarks are generated and used for facial tracking of the two or more faces of a video frame, such as the shown second video frame 702. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, any number of facial points can be determined within a frame. One or more of the other facial points that are determined can correspond to a third face. The location of the bounding box 740 can be estimated, where the estimating can be based on the location of the generated bounding box 720 shown in the prior frame 700. The three facial points shown, facial points 742, 744, and 746, might lie within the bounding box 740 or might not lie partially or completely outside the bounding box 740. For example, the second face 734 might have moved between the first video frame 700 and the second video frame 702. Based on the accuracy of the estimating of the bounding box 740, a new estimation can be determined for a third, future frame from the video, and so on. The evaluation can be performed, all or in part, on semiconductor based logic.

Figure 8:
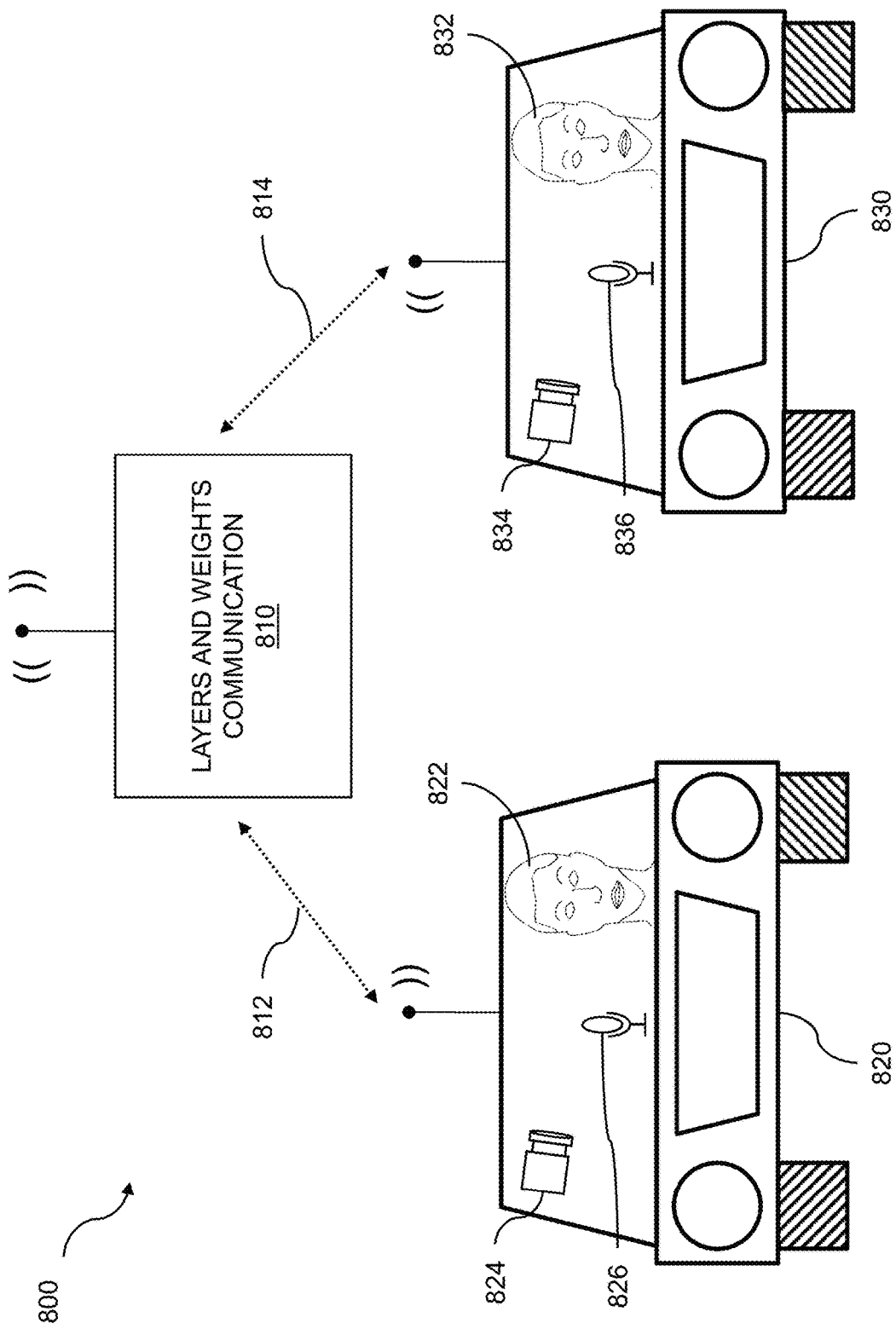
FIG. 8 is a system diagram for vehicle artificial intelligence evaluation.

FIG. 8 is a system diagram for vehicle artificial intelligence evaluation. Cameras, microphones, and other sensors can be used for collecting mental state data or cognitive state data from a general population. The collection of mental state data can be based on sporadic collection of affect data within a vehicle. The mental or cognitive state data can include facial data, voice data, physiological data, and so on. The mental state data that is collected can be used for learning layers, weights, and biases of a deep neural network. The layers, weights, and biases of the deep neural network can be used for directed control transfer for autonomous vehicles, where the directed control transfer can be between the vehicle and an individual. The transfer of control can be based on the state of operation of the vehicle, such as autonomous operation, manual operation, etc., and a condition of the individual. The condition of the individual can include being alert, engaged, impaired, asleep, unconscious, reclined, drowsy, fatigued, inattentive, or exhibiting antisocial behavior. A system diagram for vehicle artificial intelligence evaluation of mental state analysis 800 is shown. The system can include mental state data, mental state information, and layers and weights communication 810. The communicating mental state data can include mental state data, including image data and audio data, that can be collected from an individual. The communicating of the layers and weights can include sending adjusted levels and adjusted weights to a first vehicle 820, to a second vehicle 830, and so on.

The layers and weights can be sent to a first vehicle 820 using a network such as a wireless link 812 or other data transfer technique. The mental state or cognitive state data and information can be sent over the same wireless link 812 or a different wireless link. The layers and weights that can be sent can be based on mental state data including facial data from an occupant 822 of the vehicle 820. The mental state data including facial data can be collected using a camera 824 or other image capture technique. The system 800 can include collecting voice data and augmenting the mental state data with the voice data. The voice data can be collected from the occupant 822 using a microphone 826 or other audio capture technique. The voice data can include audio data, where the audio data can include traffic sounds, road noise, music that can be played by the occupant, and so on. The system 800 can include evaluating the voice data for timbre, prosody, vocal register, vocal resonance, pitch, loudness, speech rate, or language content. The evaluating voice data can also be used in evaluating the mental state or states of the occupant 822 of the vehicle 820. In embodiments, the augmenting can be based on lexical analysis of the voice data that considers sentiment. As for the first vehicle, the mental state profile can be sent to a second vehicle 830 using a wireless link 814 or other data transfer technique. The mental state profile can be based on mental state data including facial data from an occupant 832 of the vehicle 830, can be based on the mental state data including facial from the occupant 822 of the first vehicle 820, and so on. The mental state data including facial data can be collected using a camera 834 or other image capture technique. The system 800 can include collecting voice data from the occupant 832 using a microphone 836 or other audio capture technique.

Figure 9:
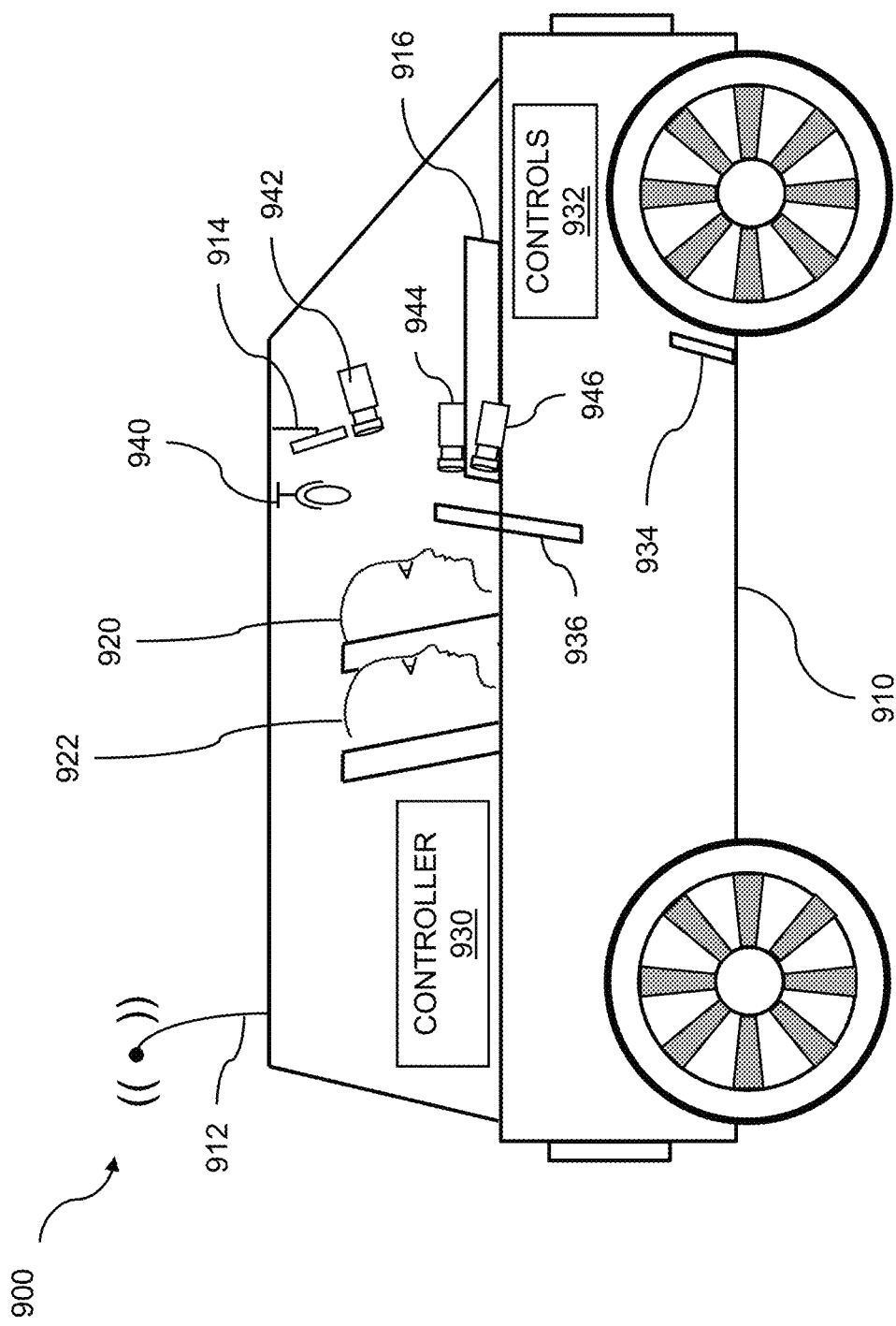
FIG. 9 is a system diagram for an interior of a vehicle.

FIG. 9 is a system diagram for an interior of a vehicle 900. Mental state analysis can be based on sporadic collection of affect data within a vehicle. Mental state data of a vehicle occupant is collected within a vehicle on an intermittent basis where the mental state data includes facial image data and the facial image data is collected intermittently across a plurality of devices within the vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include communicating with an automated assistant using audio or an avatar display. The rendering can include communicating with a vehicle navigation component for manipulating the vehicle. The rendering can include communicating the output to a second vehicle where the second vehicle is used by the occupant. One or more occupants of a vehicle 910, such as occupants 920 and 922, can be observed using a microphone 940, one or more cameras 942, 944, or 946, and other audio and image capture techniques. The image data can include video data. The video data and the audio data can include mental state data, cognitive state data, emotional state data, etc., where the mental or cognitive state data can include facial data, voice data, physiological data, and the like. The occupant can be a driver 920 of the vehicle 910, a passenger 922 within the vehicle, and so on.

The cameras or imaging devices that can be used to obtain images including facial data from the occupants of the vehicle 910 can be positioned to capture the face of the vehicle operator, the face of a vehicle passenger, multiple views of the faces of occupants of the vehicle, and so on. The cameras can be located near a rear-view mirror 914 such as camera 942, positioned near or on a dashboard 916 such as camera 944, positioned within the dashboard such as camera 946, and so on. The microphone or audio capture device 940 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 910 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 910 can include standard controls such as a steering wheel 936, a throttle control (not shown), a brake 934, and so on. The interior of the vehicle can include other controls 932 such as controls for seats, mirrors, climate controls, audio systems, etc. The controls 932 of the vehicle 910 can be operated by a controller 930. The controller 930 can control the vehicle 910 in various manners such as autonomously, semi-autonomously, assertively to a vehicle occupant 920 or 922, etc. In embodiments, the controller provides vehicle control or manipulation techniques, assistance, etc. The controller 930 can receive instructions via an antenna 912 or using other wireless techniques. The controller 930 can be preprogrammed to cause the vehicle to follow a specific route. The specific route that the vehicle is programmed to follow can be based on the cognitive state of the vehicle occupant. The specific route can be chosen based on lowest stress, least traffic, most scenic view, shortest route, and so on.

Figure 10:
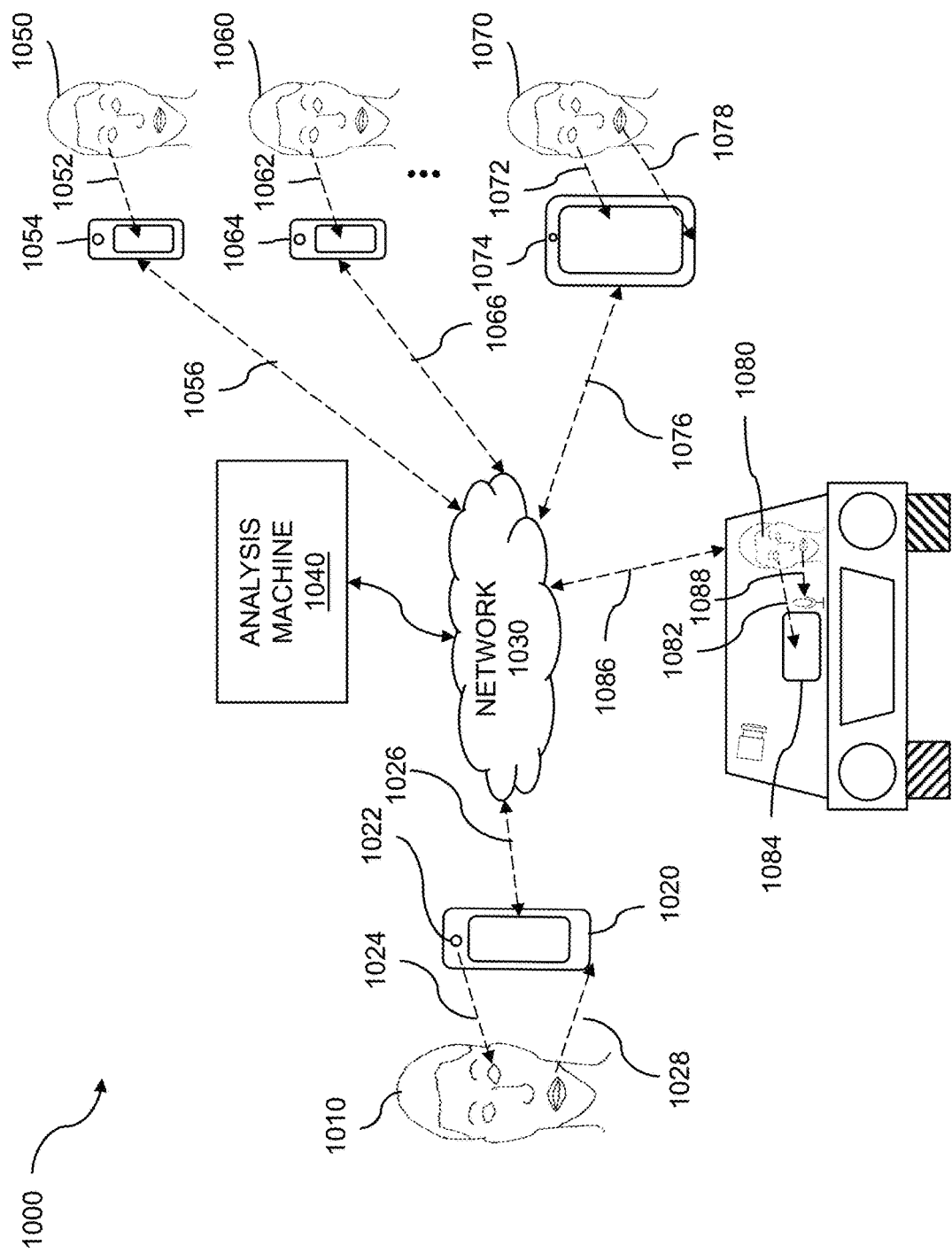
FIG. 10 shows live streaming of social video and audio.

FIG. 10 shows an example of live streaming of social video and audio. The streaming of social video and social audio can include sporadic collection of affect data within a vehicle. The live streaming can include mental state data, cognitive state data, image data, facial data, speech data, audio data, physiological data, etc. Mental state data of a vehicle occupant is collected within a vehicle on an intermittent basis. The mental state data includes facial image data and the facial image data is collected intermittently across multiple devices within the vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include communicating with an automated assistant using audio or an avatar display. The rendering can include communicating with a vehicle navigation component for manipulating the vehicle. The rendering can include communicating the output to a second vehicle where the second vehicle is used by the occupant.

The live streaming and image analysis 1000 can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences can be scheduled, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 1000 shows a user 1010 broadcasting a video live stream and an audio live stream to one or more people as shown by a first person 1050, a second person 1060, a third person 1070, and a fourth person 1080. A portable, network-enabled, electronic device 1020 can be coupled to a front-facing camera 1022. The portable electronic device 1020 can be a smartphone, a PDA, a tablet, a laptop computer, and so on. The camera 1022 coupled to the device 1020 can have a line-of-sight view 1024 to the user 1010 and can capture video of the user 1010. The portable electronic device 1020 can be coupled to a microphone (not shown). The microphone can capture voice data 1028 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 1040 using a network link 1026 to the network 1030. The network link can be a wireless link, a wired link, and so on. The recommendation engine 1040 can recommend to the user 1010 an app and/or platform that can be supported by the server and can be used to provide a video live stream, an audio live stream, or both a video live stream and an audio live stream to one or more followers of the user 1010.

In the example 1000, the user 1010 has four followers: a first person 1050, a second person 1060, a third person 1070, and a fourth person 1080. Each follower has a line-of-sight view to a video screen on a portable, networked electronic device. In other embodiments, one or more followers follow the user 1010 using any other networked electronic device, including a computer. In the example 1000, a first person 1050 has a line-of-sight view 1052 to the video screen of a device 1054; a second person 1060 has a line-of-sight view 1062 to the video screen of a device 1064, a third person 1070 has a line-of-sight view 1072 to the video screen of a device 1074, and a fourth person 1080 has a line-of-sight view 1082 to the video screen of a device 1084. The device 1074 can also capture audio data 1078 from the third person 1070, and the device 1084 can further capture audio data 1088 from the fourth person 1080. The portable electronic devices 1054, 1064, 1074, and 1084 can each be a smartphone, a PDA, a tablet, and so on. Each portable device can receive the video stream and the audio stream being broadcast by the user 1010 through the network 1030 using the app and/or platform that can be recommended by the recommendation engine 1040. The network can include the Internet, a computer network, a cellular network, and the like. The device 1054 can receive a video stream and the audio stream using the network link 1056, the device 1064 can receive a video stream and the audio stream using the network link 1066, the device 1074 can receive a video stream and the audio stream using the network link 1076, the device 1084 can receive a video stream and the audio stream using the network link 1086, and so on. The network link can be a wireless link, a wired link, a hybrid link, and the like. Depending on the app and/or platform that can be recommended by the analysis engine 1040, one or more followers, such as the followers shown 1050, 1060, 1070, and 1080, can reply to, comment on, or otherwise provide feedback to the user 1010 using their respective devices 1054, 1064, 1074, and 1084.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision making. These AUs can be used to recognize emotions experienced by the person who is being observed. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 11:
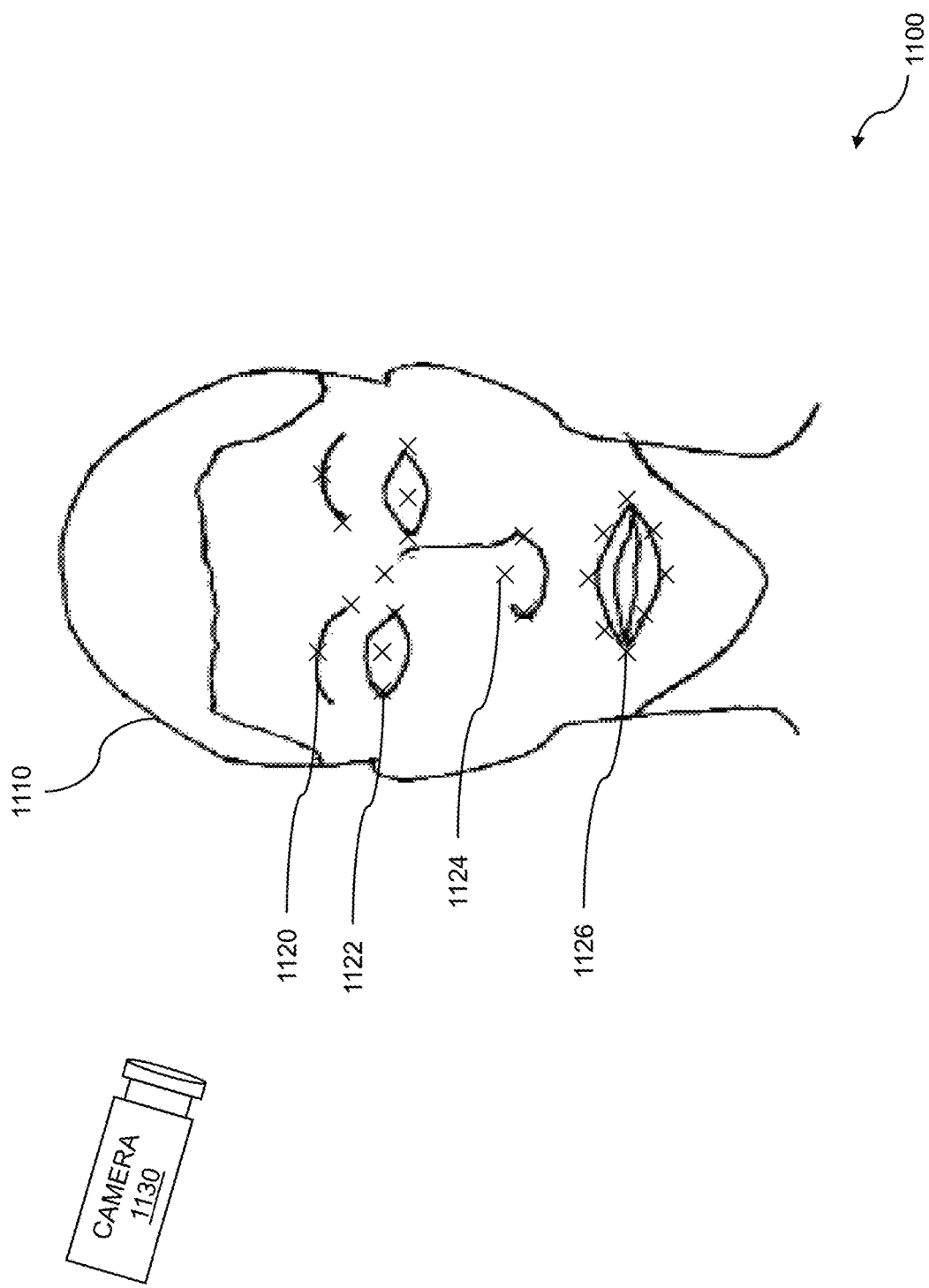
FIG. 11 shows example facial data collection including landmarks.

FIG. 11 shows example facial data collection including landmarks. Features of a face or a plurality of faces can be extracted from sporadically collected mental state data using mental state analysis. The mental state data can include affect data. The sporadically collected mental state data further can include facial image data, audio information, physiological information, and so on. The mental state analysis can be used for sporadic collection of affect data within a vehicle. An output can be rendered based on the analysis of the mental state data. The rendering can include communication by a virtual assistant, where the virtual assistant can communicate via audio, an avatar display, etc. The rendering can include communicating with a navigation component within the vehicle, where the vehicle can be operated in an autonomous mode. The mental state analysis can include translating the mental state data into an emoji for representation of the occupant. Further embodiments include analyzing the mental state data to determine a cognitive state.

Facial data including facial landmarks can be collected 1100 using a variety of electronic hardware and software techniques. A face 1110 can be observed using a camera 1130 in order to collect facial data that includes facial landmarks. The facial data can be collected from a plurality of people using one or more of a variety of cameras. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend, for example, on the position of the camera 1130 relative to the face 1110, the number of cameras used, the illumination of the face, etc. For example, if the face 1110 is poorly lit or over-exposed (e.g. in an area of bright light), the processing of the facial data to identify facial landmarks might be rendered more difficult. In another example, the camera 1130 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 1120, an outer eye edge 1122, a nose 1124, a corner of a mouth 1126, and so on. Any number of facial landmarks can be identified from the facial data that is captured. The facial landmarks that are identified can be analyzed to identify facial action units. For example, the action units that can be identified can include AU02 outer brow raiser, AU14 dimpler, AU17 chin raiser, and so on. Any number of action units can be identified. The action units can be used alone and/or in combination to infer one or more mental states and emotions. A similar process can be applied to gesture analysis (e.g. hand gestures) with all of the analysis being accomplished or augmented by a mobile device, a server, semiconductor-based logic, and so on.

Figure 12:
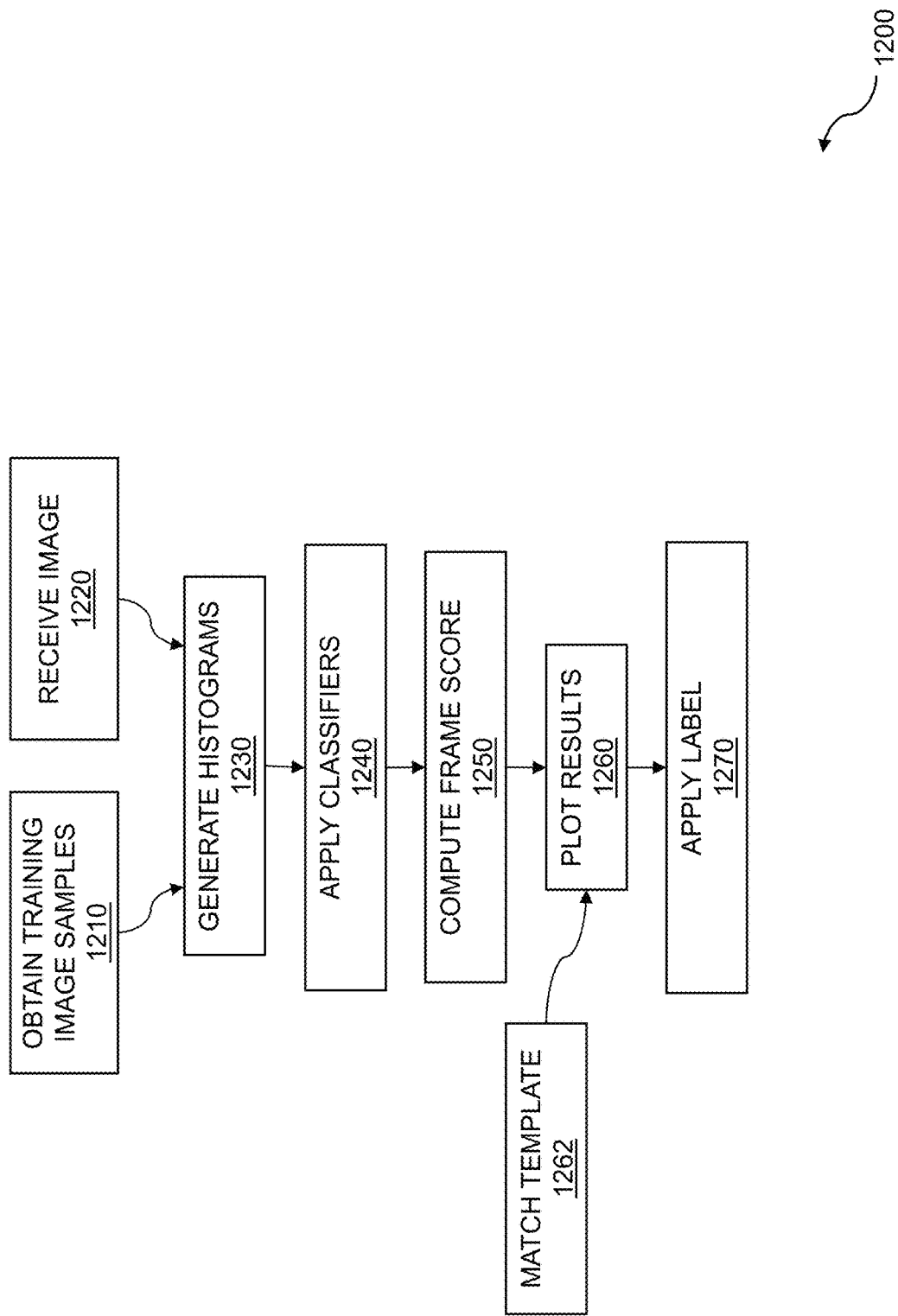
FIG. 12 is a flow diagram for detecting facial expressions.

FIG. 12 is a flow diagram for detecting facial expressions. Features of a face or a plurality of faces can be extracted from sporadically collected video data, audio data, physiological data, and so on. The sporadically collected data can include affect data, where the affect data is sporadically collected within a vehicle. The mobile affect data can be rendered based on the mental state data. The rendering can include communication by a virtual assistant, where the virtual assistant communicates inside the vehicle via audio, an avatar display, and so on. Embodiments further include translating the mental state data into an emoji for representation of the occupant. The flow 1200, or portions thereof, can be implemented in semiconductor logic, can be accomplished using a mobile device, using a server device, and so on. The flow 1200 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU) where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1200 begins by obtaining training image samples 1210. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera. The flow 1200 continues with receiving an image 1220. The image 1220 can be received from one or more cameras. As discussed throughout, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. For example, the manipulated image and a flipped or mirrored version of the manipulated image can be analyzed alone and/or in combination to improve analysis. The flow 1200 continues with generating histograms 1230 for the training images and the one or more versions of the received image. The histograms can be generated for one or more versions of the manipulated received image. The histograms can be based on a HoG or another histogram. As described above, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example.

The flow 1200 continues with applying classifiers 1240 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. For example, the classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1200 continues with computing a frame score 1250. The score computed for an image, where the image can be a frame from a video, can be used to determine the presence of a facial expression in the image or video frame. The score can be based on one or more versions of the image 1220 or a manipulated image. For example, the score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The chosen classifier can be used to identify symmetrical facial expressions (e.g. smile), asymmetrical facial expressions (e.g. outer brow raiser), and so on.

The flow 1200 continues with plotting results 1260. The results that are plotted can include one or more scores for one or more frames computed over a given time t. For example, the plotted results can include classifier probability results from analysis of HoGs for a sequence of images and video frames. The plotted results can be matched with a template 1262. The template can be temporal and can be represented by a centered box function or another function. A best fit with one or more templates can be found by computing a minimum error. Other best-fit techniques can include polynomial curve fitting, geometric curve fitting, and so on. The flow 1200 continues with applying a label 1270. The label can be used to indicate that a particular facial expression has been detected in the one or more images or video frames which constitute the image that was received 1220. For example, the label can be used to indicate that any of a range of facial expressions has been detected, including a smile, an asymmetric smile, a frown, and so on. Various steps in the flow 1200 may be changed in order, repeated, omitted, or the like without departing from the disclosed concepts. Various embodiments of the flow 1200 can be included in a computer program product embodied in a non-transitory computer readable medium that includes code executable by one or more processors. Various embodiments of the flow 1200, or portions thereof, can be included on a semiconductor chip and implemented in special purpose logic, programmable logic, and so on.

Figure 13:
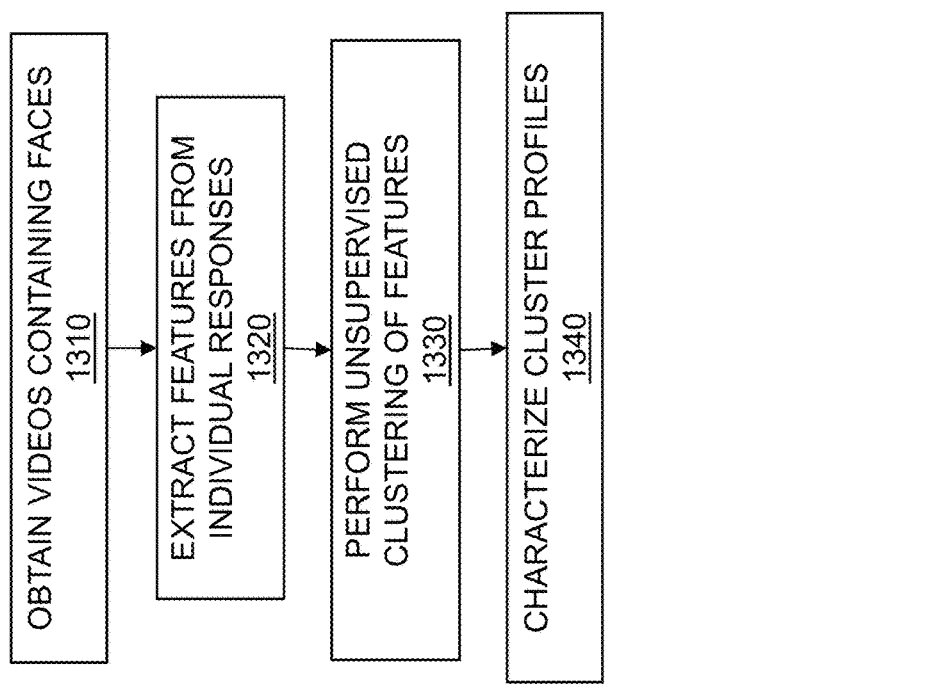
FIG. 13 is a flow diagram for the large-scale clustering of facial events.

FIG. 13 is a flow diagram for the large-scale clustering of facial events. The large-scale clustering of facial events can be used in conjunction with sporadic collection of affect data within a vehicle. The facial events can be associated with mental states. Mental state data of a vehicle occupant is collected within a vehicle on an intermittent basis where the mental state data includes facial image data and the facial image data is collected intermittently across a plurality of devices within the vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include communicating with an automated assistant using audio or an avatar display. The rendering can include communicating with a vehicle navigation component for manipulating the vehicle. The rendering can include communicating the output to a second vehicle where the second vehicle is used by the occupant.

The clustering and evaluation of facial events can be augmented using a mobile device, a server, semiconductor based logic, and so on. As discussed above, collection of facial video data from one or more people can include a web-based framework. The web-based framework can be used to collect facial video data from, for example, large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on.

The flow 1300 begins with obtaining videos containing faces 1310. The videos can be obtained using one or more cameras, where the cameras can include a webcam coupled to one or more devices employed by the one or more people using the web-based framework. The flow 1300 continues with extracting features from the individual responses 1320. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1300 continues with performing unsupervised clustering of features 1330. The unsupervised clustering can be based on an event.

The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1300 continues with characterizing cluster profiles 1340. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. For example, the number of smiles resulting from people viewing a humorous video can be compared across various demographic groups, where the groups can be formed based on geographic location, age, ethnicity, gender, and so on. Various steps in the flow 1300 may be changed in order, repeated, omitted, or the like without departing from the disclosed concepts. Various embodiments of the flow 1300 can be included in a computer program product embodied in a non-transitory computer readable medium that includes code executable by one or more processors. Various embodiments of the flow 1300, or portions thereof, can be included on a semiconductor chip and implemented in special purpose logic, programmable logic, and so on.

Figure 14:
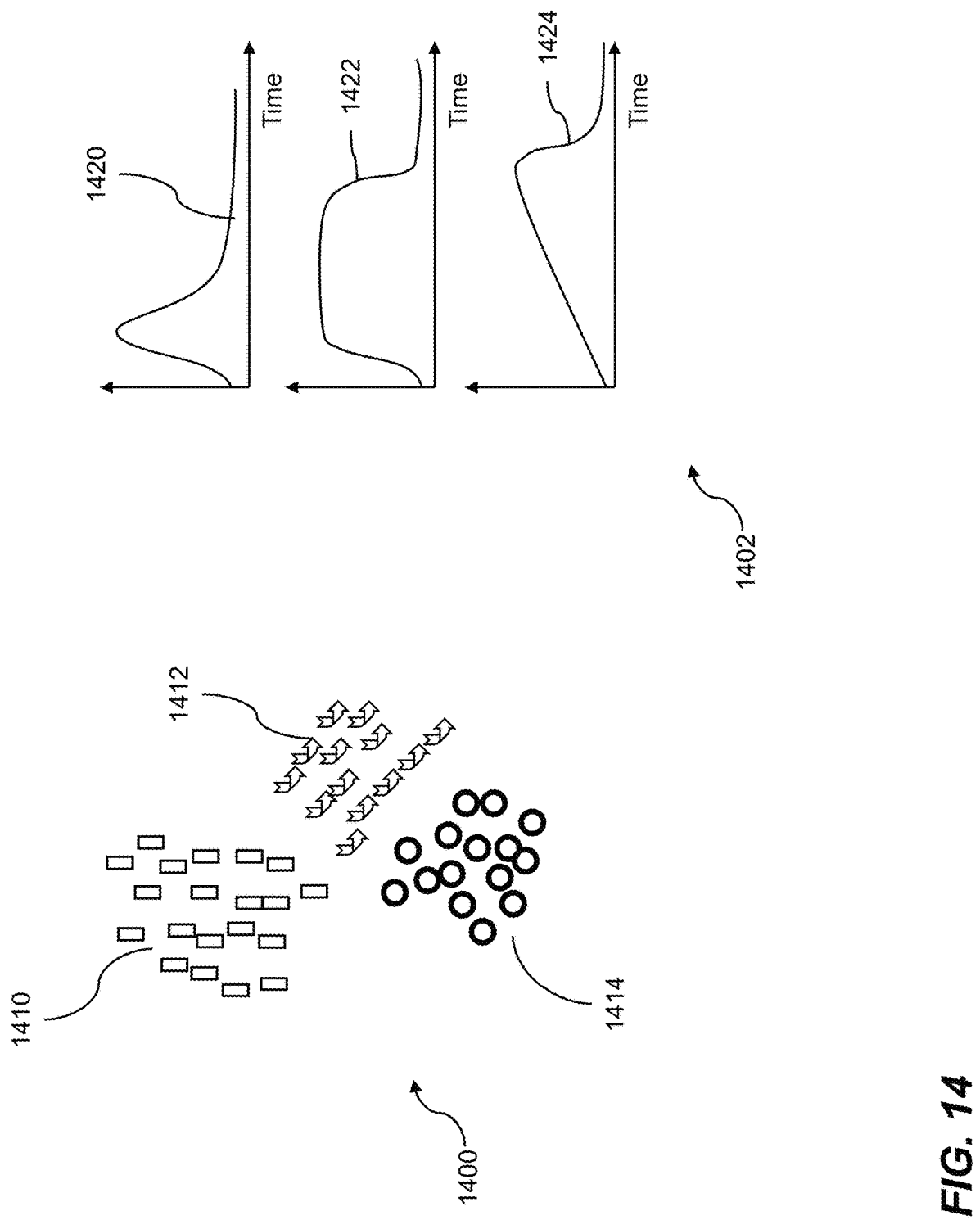
FIG. 14 shows unsupervised clustering of features and characterizations of cluster profiles.

FIG. 14 shows unsupervised clustering of features and characterizations of cluster profiles. The clustering of features and characterizations of cluster profiles can be performed for mental state analysis, where the mental state analysis can be performed for sporadic collection of affect data within a vehicle. Mental state data of a vehicle occupant is collected within a vehicle on an intermittent basis. The mental state data includes facial image data and the facial image data is collected intermittently across multiple devices within the vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include communicating with an automated assistant using audio or an avatar display. The rendering can include communicating with a vehicle navigation component for manipulating the vehicle. The rendering can include communicating the output to a second vehicle where the second vehicle is used by the occupant.

Features such as samples of facial data can be clustered using unsupervised clustering. Various clusters can be formed which include similar groupings of facial data observations. The example 1400 shows three clusters, clusters 1410, 1412, and 1414. The clusters can be based on video collected from people who have opted-in to video collection. When the data collected is captured using a web-based framework, the data collection can be performed on a grand scale, including hundreds, thousands, or even more participants who can be located nearby and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1402 can be generated based on the clusters that can be formed from unsupervised clustering, with time shown on the x-axis and intensity or frequency shown on the y-axis. The cluster profiles can be based on captured facial data, including facial expressions. The cluster profile 1420 can be based on the cluster 1410, the cluster profile 1422 can be based on the cluster 1412, and the cluster profile 1424 can be based on the cluster 1414. The cluster profiles 1420, 1422, and 1424 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 15A:
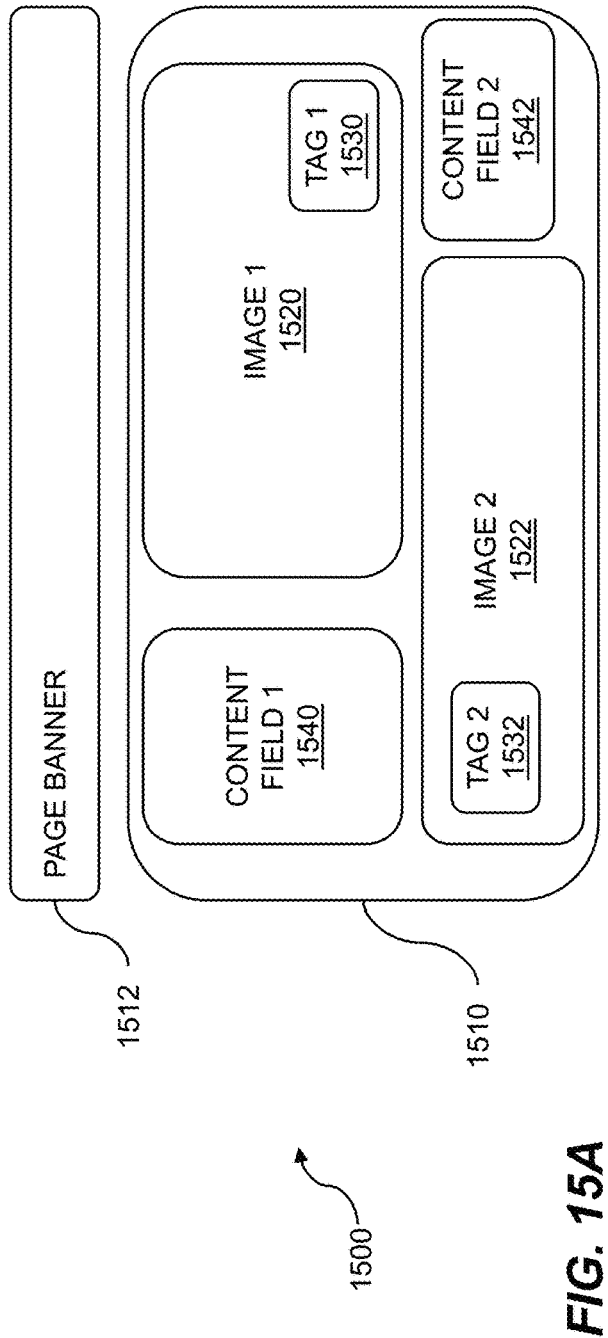
FIG. 15A shows example tags embedded in a webpage.

FIG. 15A shows example tags embedded in a webpage that can be used with sporadically collected mobile affect data. The affect data can include video data, audio data, or physiological data, and can be collected sporadically within a vehicle. Once a tag is detected, a mobile device, a server, semiconductor based logic, etc. can be used to evaluate associated facial expressions. A webpage 1500 can include a page body 1510, a page banner 1512, and so on. The page body can include one or more objects, where the objects can include text, images, videos, audio, and so on. The example page body 1510 shown includes a first image, image 1 1520; a second image, image 2 1522; a first content field, content field 1 1540; and a second content field, content field 2 1542. In practice, the page body 1510 can contain any number of images and content fields, and can include one or more videos, one or more audio presentations, and so on. The page body can include embedded tags, such as tag 1 1530 and tag 2 1532. In the example shown, tag 1 1530 is embedded in image 1 1520, and tag 2 1532 is embedded in image 2 1522. In embodiments, any number of tags can be imbedded. Tags can also be embedded in content fields, in videos, in audio presentations, etc. When a user mouses over a tag or clicks on an object associated with a tag, the tag can be invoked. For example, when the user mouses over tag 1 1530, tag 1 1530 can then be invoked. Invoking tag 1 1530 can include enabling a camera coupled to a user's device and capturing one or more images of the user as the user views a media presentation (or digital experience). In a similar manner, when the user mouses over tag 2 1532, tag 2 1532 can be invoked. Invoking tag 2 1532 can also include enabling the camera and capturing images of the user. In other embodiments, other actions are taken based on invocation of the one or more tags. For example, invoking an embedded tag can initiate an analysis technique, post to social media, award the user a coupon or another prize, initiate mental state analysis, perform emotion analysis, and so on.

Figure 15B:
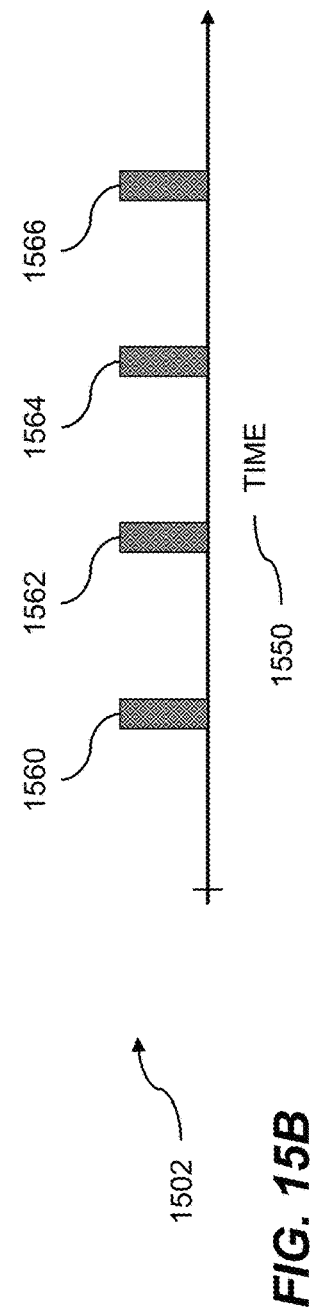
FIG. 15B shows invoking tags to collect images.

FIG. 15B shows invoking tags to collect images that can be used with sporadically collected mobile affect data, where the sporadically collected mobile affect data can be collected within a vehicle. In some embodiments, the tags can invoke collection of sporadic mental state data. As stated above, a media presentation can be a video, a webpage, and so on. A video 1502 can include one or more embedded tags, such as a tag 1560, another tag 1562, a third tag 1564, a fourth tag 1566, and so on. In practice, any number of tags can be included in the media presentation. The one or more tags can be invoked during the media presentation. The collection of the invoked tags can occur over time, as represented by a timeline 1550. When a tag is encountered in the media presentation, the tag can be invoked. For example, when the tag 1560 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1560 does not enable the camera to capture images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages, advertising messages, social media sharing, etc., and that enable the camera and image capture when invoked would be embedded in the media presentation, social media sharing, and so on. However, tags embedded in the media presentation that are related to advertisements would not enable the camera when invoked. Various other situations of tag invocation are possible.

Figure 16:
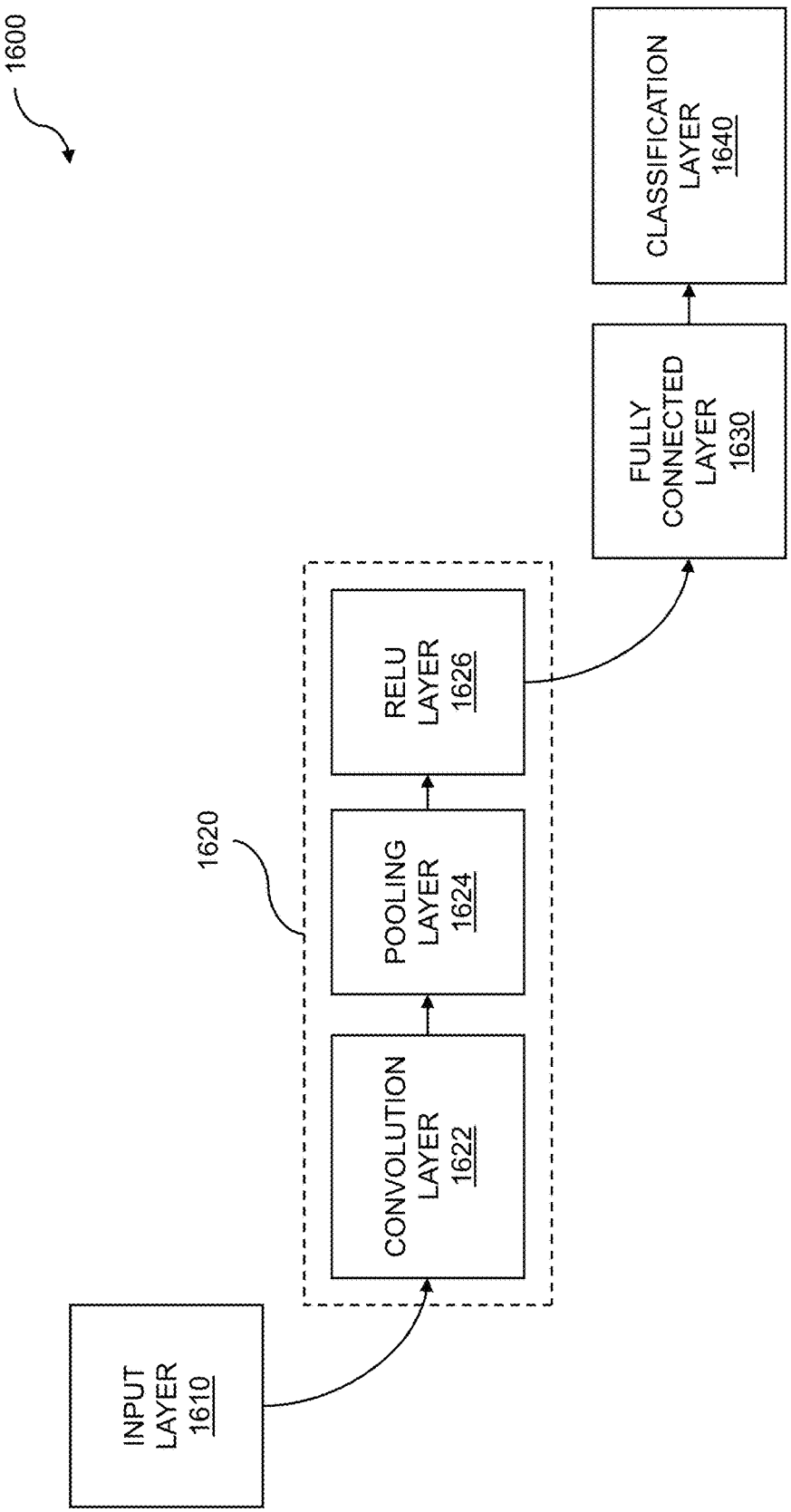
FIG. 16 is an example showing a convolutional neural network.

FIG. 16 is an example showing a convolutional neural network (CNN). A convolutional neural network such as 1600 can be used for deep learning, where the deep learning can be applied to sporadic collection of affect data within a vehicle. Mental state data of a vehicle occupant is collected within a vehicle on an intermittent basis where the mental state data includes facial image data and the facial image data is collected intermittently across a plurality of devices within the vehicle. A plurality of images can be collected. Audio information is also collected. Processors are used for interpolating mental state data in between the collecting which is intermittent. Additional data is imputed. Analysis of the mental state data on the vehicle occupant is obtained, where the analysis of the mental state data includes analyzing the facial image data. An output is rendered based on the analysis of the mental state data. The rendering can include communicating with a personal assistant, manipulating the vehicle, or translating the mental state data into an emoji. The convolutional neural network can be applied to analysis tasks such as cognitive state analysis, mental state analysis, mood analysis, emotional state analysis, and so on. The CNN can be applied to communication tasks such as providing audio communication with the vehicle occupant, providing an avatar display, and the like. Cognitive state data can include mental processes, where the mental processes can include attention, creativity, memory, perception, problem solving, thinking, use of language, or the like.

Cognitive or mental analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to act to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 16 is an example showing a convolutional neural network 1600. The convolutional neural network can be used for deep learning, where the deep learning can be applied to cognitive state based vehicle manipulation using near-infrared image processing. The deep learning system can be accomplished using a convolution neural network or other techniques. The deep learning can accomplish facial recognition and analysis tasks. The network includes an input layer 1610. The input layer 1610 receives image data. The image data can be input in a variety of formats, such as JPEG, TIFF, BMP, and GIF. Compressed image formats can be decompressed into arrays of pixels, wherein each pixel can include an RGB tuple. The input layer 1610 can then perform processing such as identifying boundaries of the face, identifying landmarks of the face, extracting features of the face, and/or rotating a face within the plurality of images.

The network includes a collection of intermediate layers 1620. The multilayered analysis engine can include a convolutional neural network. Thus, the intermediate layers can include a convolution layer 1622. The convolution layer 1622 can include multiple sublayers, including hidden layers within it. The output of the convolution layer 1622 feeds into a pooling layer 1624. The pooling layer 1624 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 165-percent of the downstream node activations. The multilayered analysis engine can further include a max pooling layer 1624. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1626. The output of the pooling layer 1624 can be input to the RELU layer 1626. In embodiments, the RELU layer implements an activation function such as $f(x)-\max(0,x)$, thus providing an activation with a threshold at zero. In some embodiments, the RELU layer 1626 is a leaky RELU layer. In this case, instead of the activation function providing zero when x<0, a small negative slope is used, resulting in an activation function such as $f(x)=1(x<0)(ax)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1622 and one or more hidden layers, and wherein the multilayered analysis engine can be used for emotional analysis.

The example 1600 includes a fully connected layer 1630. The fully connected layer 1630 processes each pixel/data point from the output of the collection of intermediate layers 1620. The fully connected layer 1630 takes all neurons in the previous layer and connects them to every single neuron it has. The output of the fully connected layer 1630 provides input to a classification layer 1640. The output of the classification layer 1640 provides a facial expression and/or cognitive state as its output. Thus, a multilayered analysis engine such as the one depicted in FIG. 16 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy; whether a voice is female, male, or robotic; whether a message is legitimate email or a "spam" message; and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect, the person spending more time playing an online game or navigating a webpage, the person converting by buying a product or service, and so on. The reinforced learning can be based on exploring a solution space and adapting the model, algorithm, etc., which stem from outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 17:
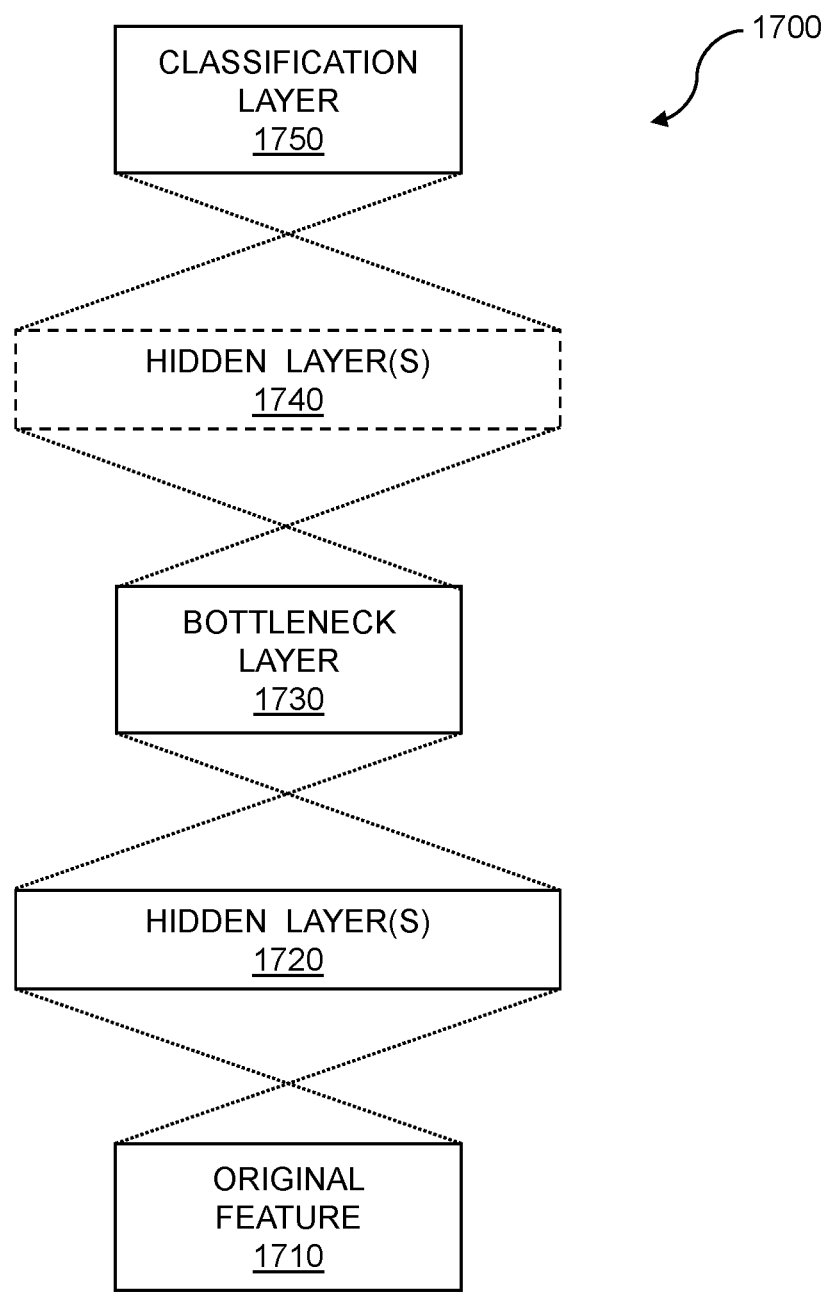
FIG. 17 illustrates a bottleneck layer within a deep learning environment.

FIG. 17 illustrates a bottleneck layer within a deep learning environment. A plurality of layers in a deep neural network (DNN) can include a bottleneck layer. The deep learning environment can be used for analysis of sporadic affect data collected within a vehicle. A deep neural network can apply classifiers such as image classifiers, facial classifiers, audio classifiers, speech classifiers, physiological classifiers, and so on. The classifiers can be learned by analyzing cognitive state data, mental state data, emotional state data, and so on. Mental state data of a vehicle occupant is collected within a vehicle on an intermittent basis where the mental state data includes facial image data which is collected intermittently across a plurality of devices within the vehicle. Processors are used to interpolate mental state data in between the collecting which is intermittent. Analysis of the mental state data on the vehicle occupant is obtained, where the analysis of the mental state data includes analyzing the facial image data. An output is rendered based on the analysis of the mental state data. The rendering can include communicating with an automated assistant using audio or an avatar display. The rendering can include communicating with a vehicle navigation component for manipulating the vehicle. The rendering can include communicating the output to a second vehicle where the second vehicle is used by the occupant.

Layers of a deep neural network can include a bottleneck layer 1700. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1710. A feature such as an image feature can include points, edges, objects, boundaries between and among regions, properties, and so on. The deep neural network can include one or more hidden layers 1720. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1730. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1740. The number of the hidden layers can include zero hidden layers, one hidden layer, a plurality of hidden layers, and so on. The hidden layers following the bottleneck layer can include more nodes than the bottleneck layer. The deep neural network can include a classification layer 1750. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 18:
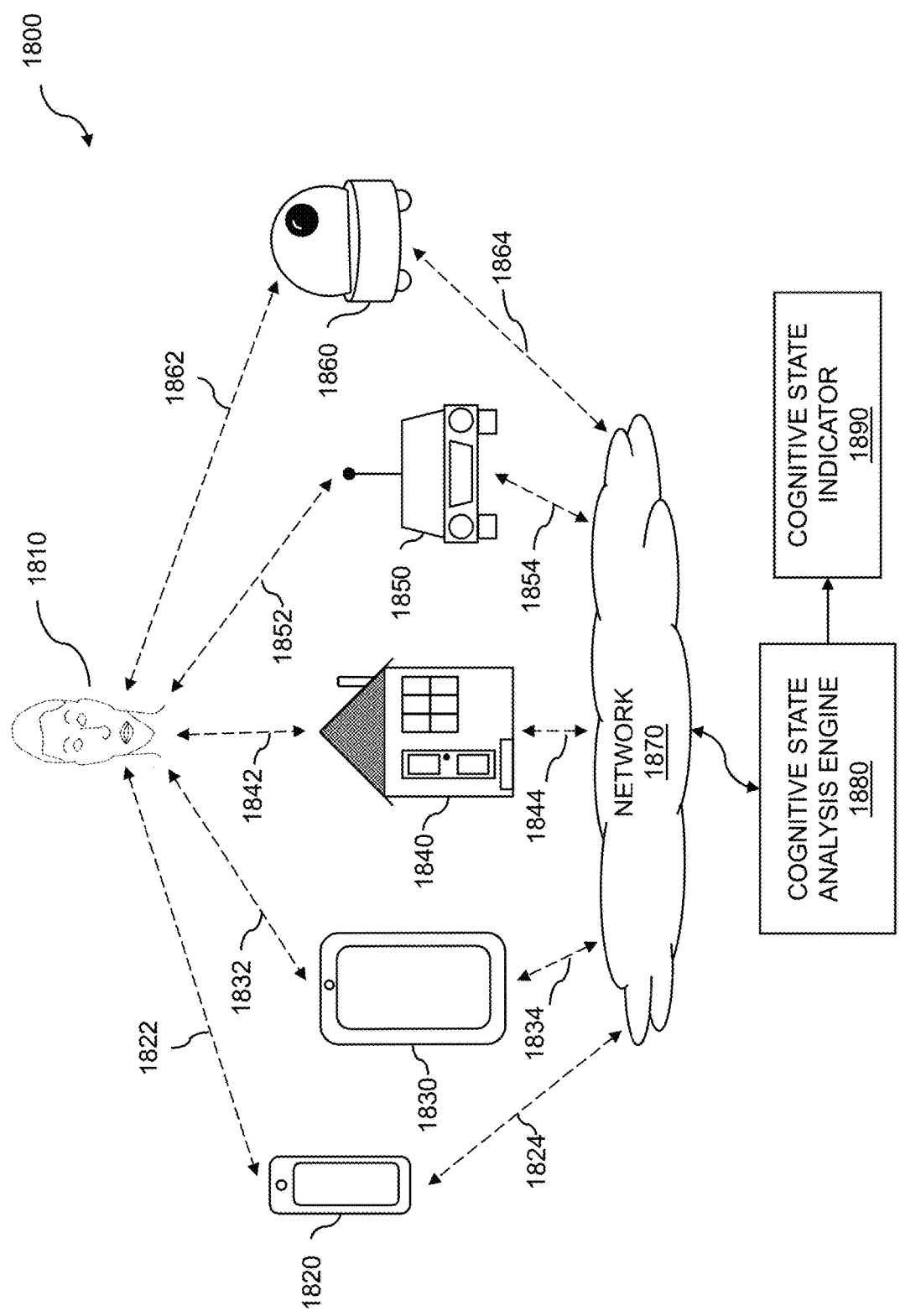
FIG. 18 shows data collection including devices and locations.

FIG. 18 shows data collection including devices and locations 1800. Data, including video data, audio data and physio data, can be collected sporadically within a vehicle. The data can be obtained from multiple devices, vehicles, and locations. Mental state data of a vehicle occupant is collected within a vehicle on an intermittent basis where the mental state data includes facial image data which is collected intermittently across a plurality of devices within the vehicle. Audio information is also collected. Processors are used for interpolating mental state data in between the collecting which is intermittent. Additional data is imputed. Analysis of the mental state data on the vehicle occupant is obtained, where the analysis of the mental state data includes analyzing the facial image data. An output is rendered based on the analysis of the mental state data. The rendering can include communicating with a personal assistant, manipulating the vehicle, or translating the mental state data into an emoji.

The multiple mobile devices, vehicles, and locations 1800 can be used separately or in combination to collect video data on a user 1810. The video data can include facial data. Other data such as audio data, physiological data, and so on, can be collected on the user. While one person is shown, the video data, or other data, can be collected on multiple people. A user 1810 can be observed as she or he is performing a task, experiencing an event, viewing a media presentation, and so on. The user 1810 can be shown one or more media presentations, political presentations, social media, or another form of displayed media. The one or more media presentations can be shown to a plurality of people. The media presentations can be displayed on an electronic display coupled to a client device. The data collected on the user 1810 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1810 can be analyzed and viewed for a variety of purposes including expression analysis, mental state analysis, cognitive state analysis, and so on. The electronic display can be on a smartphone 1820 as shown, a tablet computer 1830, a personal digital assistant, a television, a mobile monitor, or any other type of electronic device. In one embodiment, expression data is collected on a mobile device such as a cell phone 1820, a tablet computer 1830, a laptop computer, or a watch. Thus, the multiple sources can include at least one mobile device, such as a phone 1820 or a tablet 1830, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1810, data can be collected in a house 1840 using a web camera or the like; in a vehicle 1850 using a web camera, client device, etc.; by a social robot 1860, and so on.

As the user 1810 is monitored, the user 1810 might move due to the nature of the task, boredom, discomfort, distractions, or for another reason. As the user moves, the camera with a view of the user's face can be changed. Thus, as an example, if the user 1810 is looking in a first direction, the line of sight 1822 from the smartphone 1820 is able to observe the user's face, but if the user is looking in a second direction, the line of sight 1832 from the tablet 1830 is able to observe the user's face. Furthermore, in other embodiments, if the user is looking in a third direction, the line of sight 1842 from a camera in the house 1840 is able to observe the user's face, and if the user is looking in a fourth direction, the line of sight 1852 from the camera in the vehicle 1850 is able to observe the user's face. If the user is looking in a fifth direction, the line of sight 1862 from the social robot 1860 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1810 can also use a wearable device including a camera for gathering contextual information and/or collecting expression data on other users. Because the user 1810 can move her or his head, the facial data can be collected intermittently when she or he is looking in a direction of a camera. In some cases, multiple people can be included in the view from one or more cameras, and some embodiments include filtering out faces of one or more other people to determine whether the user 1810 is looking toward a camera. All or some of the expression data can be continuously or sporadically available from the various devices and other devices.

The captured video data can include cognitive content, such as facial expressions, etc., and can be transferred over a network 1870. The network can include the Internet or other computer network. The smartphone 1820 can share video using a link 1824, the tablet 1830 using a link 1834, the house 1840 using a link 1844, the vehicle 1850 using a link 1854, and the social robot 1860 using a link 1864. The links 1824, 1834, 1844, 1854, and 1864 can be wired, wireless, and hybrid links. The captured video data, including facial expressions, can be analyzed on a cognitive state analysis engine 1880, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1890. The cognitive state indicator 1890 can indicate cognitive states, mental states, moods, emotions, etc. In embodiments, the mental state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 19:
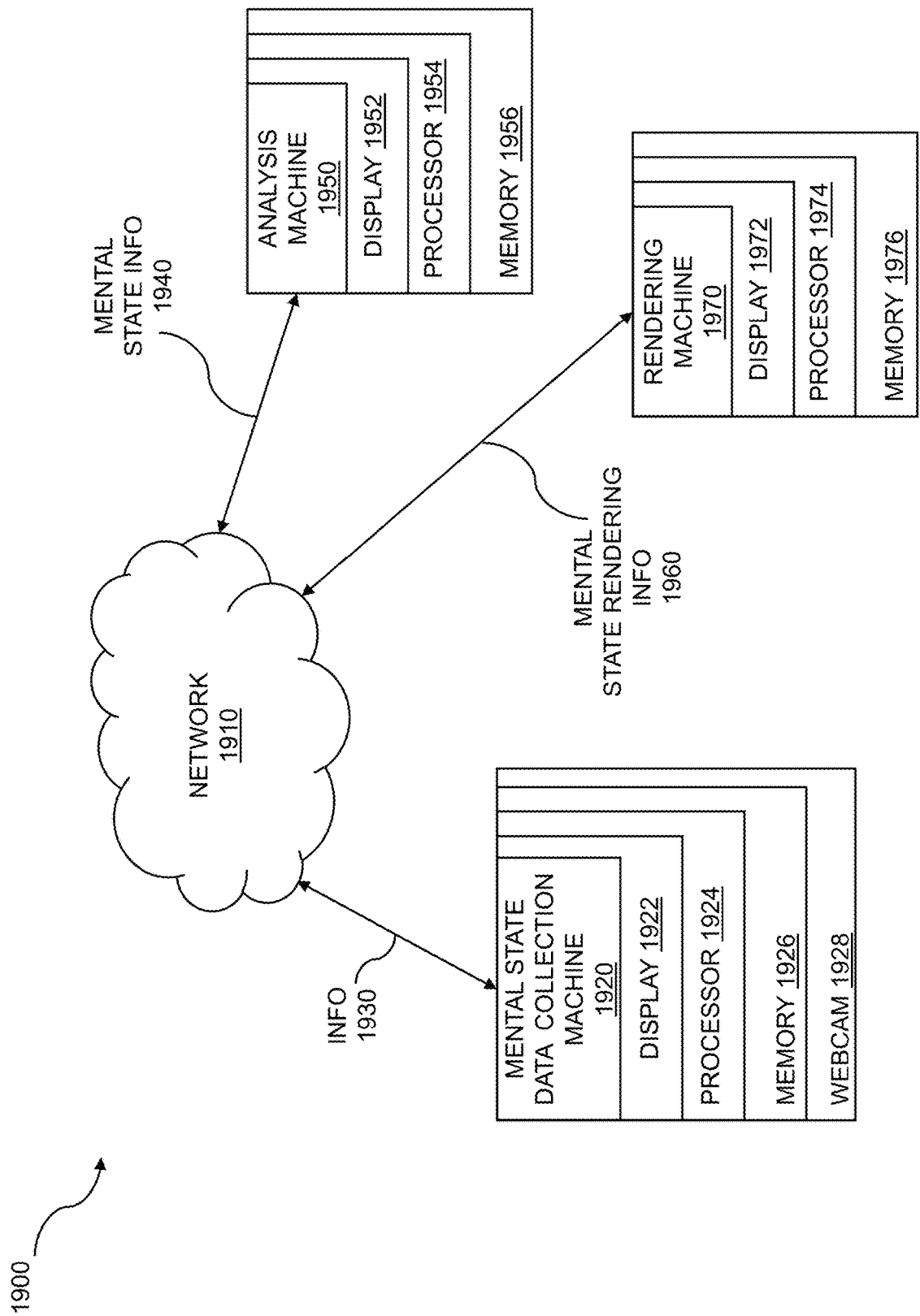
FIG. 19 is a system diagram for mental state analysis.

FIG. 19 is a system diagram for mental state analysis. A system 1900 can be used for sporadic collection of mental state data with mobile affect data. The affect data can be collected sporadically within a vehicle. The system 1900 may include a mental state data collection machine 1920 and an analysis machine 1950. The mental state data collection machine 1920 may be configured to collect the mental state data of vehicle occupant on an intermittent basis. The mental state data collection machine 1920 may include a display 1922; one or more processors 1924; a memory 1926 designed to store mental state data, instructions, and the like; and a webcam 1928. The mental state data collection can include one or more microphones (not shown) for collecting audio information. The display 1922 may be any electronic display, including but not limited to, a computer display, a laptop screen, a netbook screen, a tablet computer screen, a cell phone display, a mobile device display, a remote with a display, a television, a projector, or the like. The webcam 1928 may comprise a camera on a computer (such as a laptop, a netbook, a tablet, or the like), a video camera, a still camera, a cell phone camera, a mobile device camera (including, but not limited to, a forward-facing camera), a thermal imager, a CCD device, a three-dimensional camera, a depth camera, and multiple webcams used to capture different views of viewers or any other type of image capture apparatus that may allow image data captured to be used by an electronic system. The mental state data collection machine 1920 may be configured to transmit mental state information 1930 to a server 1950 via a network 1910 such as the Internet or another network.

The analysis machine 1950 may be configured to obtain analysis of the mental state data on the individual and render an output based on the analysis of the mental state data. The analysis machine 1950 may obtain mental state information 1940 from the network 1910 and may be configured as a web service. In some embodiments, the analysis machine 1950 may send the analysis of the mental state data to another machine, such as the mental state data collection machine 1920, so that the analysis of the mental state data may be received from a web service. The analysis machine 1950 may include a display 1952, one or more processors 1954, and a memory 1956 designed to store system information, instructions, and the like. The display 1952 may be any electronic display, including but not limited to, a computer display, a laptop screen, a netbook screen, a tablet computer screen, a cell phone display, a mobile device display, a remote with a display, a television, a projector, or the like. The one or more processors 1954, when executing the instructions which are stored, can be configured to analyze mental state information 1940 that may be received from the mental state data collection machine 1920. In some embodiments, the functions of the mental state data collection machine 1920 and the analysis machine 1950 may be combined into a single computer. In some embodiments, the rendering of mental state analysis can occur on a different computer from the collection machine 1920 or the analysis machine 1950. This computer may be a rendering machine 1970 which receives data or information 1930, mental state information 1940 from the analysis machine 1950, or both, and may be considered mental state rendering information 1960. In embodiments, the rendering machine 1970 includes one or more processors 1974 coupled to a memory 1976, and a display 1972. The rendering may include generation and display of emoticons. The rendering can include translating the mental state data into an emoji for representation of the individual. The rendering can include communication by a virtual assistant. The virtual assistant can communicate with one or more vehicle occupants using audio, video, haptics, and the like. The virtual assistant can include an avatar display, where the avatar display can be rendered on a display or screen within the vehicle, on a display coupled to a personal electronic device, and so on. The rendering can include communicating with a navigation component of the vehicle. The navigation component can include a GPS, vehicle controls, etc. In embodiments, the rendering can include manipulating the vehicle, where the vehicle can be an autonomous vehicle, a semi-autonomous vehicle, etc. In other embodiments, the rendering can include communicating the output to a second vehicle, where the second vehicle can be used by the occupant. The rendering can include configuring the second vehicle, permitting access to the second vehicle, manipulating the second vehicle, and the like.

In embodiments, a computer program product is embodied in a non-transitory computer readable medium for mental state analysis, the computer program product comprising code which causes one or more processors to perform operations of: collecting mental state data of a vehicle occupant within a vehicle on an intermittent basis wherein the mental state data includes facial image data and the facial image data is collected intermittently across a plurality of devices within the vehicle; interpolating, using one or more processors, mental state data in between the collecting which is intermittent; obtaining analysis of the mental state data on the vehicle occupant, wherein the analysis of the mental state data includes analyzing the facial image data; and rendering an output based on the analysis of the mental state data.

Each of the above methods may be executed on one or more processors on one or more computer systems. Embodiments may include various forms of distributed computing, client/server computing, mesh computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples but is to be understood in the broadest sense allowable by law.

What is claimed is:

1. A computer-implemented method for mental state analysis comprising:
  collecting mental state data of a vehicle occupant within a vehicle on an intermittent basis wherein the mental state data includes facial image data and the facial image data is collected intermittently, when the occupant is looking in a direction of a camera, across a plurality of devices within the vehicle;
  interpolating, using one or more processors, mental state data in between the collecting which is intermittent, wherein the intermittent mental state data is interpolated to fill in gaps in the collected mental state data;

obtaining analysis of the mental state data on the vehicle occupant, wherein the analysis of the mental state data includes analyzing the mental state data that was interpolated; and rendering an output based on the analysis of the mental state data, wherein the rendering includes communicating with a navigation component of the vehicle.

2. The method of claim 1 wherein the collecting mental state data further includes collecting audio information on the vehicle occupant.

3. The method of claim 2 wherein the audio information is intermittent.

4. The method of claim 3 wherein the audio information includes speech.

5. The method of claim 3 wherein the audio information includes non-speech vocalizations.

6. The method of claim 2 wherein the audio information is collected from a plurality of microphones.

7. The method of claim 1 further comprising imputing additional mental state data where the mental state data is missing.

8. The method of claim 7 wherein the imputing is based on mental state data collected from other individuals associated with the vehicle occupant.

9. The method of claim 1 wherein the collecting mental state data includes collecting a plurality of images.

10. The method of claim 9 wherein the plurality of images includes near-infrared images.

11. The method of claim 1 wherein the rendering includes communication by a virtual assistant.

12. The method of claim 1 wherein the rendering includes manipulating the vehicle.

13. The method of claim 12 wherein the manipulating the vehicle includes operating the vehicle in autonomous mode.

14. The method of claim 1 wherein the rendering includes communicating the output to a second vehicle.

15. The method of claim 14 wherein the second vehicle is used by the occupant.

16. The method of claim 1 wherein the facial image data is obtained from a series of images of the occupant.

17. The method of claim 16 further comprising identifying a second face from a second individual within the series of images.

18. The method of claim 17 further comprising tracking the second face within the series of images.

19. The method of claim 17 further comprising analyzing the second face for mental state data.

20. The method of claim 16 further comprising tracking a face for the occupant within the series of images.

21. The method of claim 1 further comprising collecting other mental state data from the occupant on a continuous basis.

22. The method of claim 21 wherein the other mental state data comprises audio data.

23. The method of claim 1 wherein the mental state data of an occupant on an intermittent basis includes audio voice data.

24. The method of claim 1 further comprising analyzing the mental state data to determine a cognitive state.

25. The method of claim 1 further comprising obtaining additional images of one or more additional occupants of the vehicle, wherein the additional images are analyzed to determine one or more additional cognitive states.

26. A computer program product embodied in a non-transitory computer readable medium for mental state analysis, the computer program product comprising code which causes one or more processors to perform operations of:

collecting mental state data of a vehicle occupant within a vehicle on an intermittent basis wherein the mental state data includes facial image data and the facial image data is collected intermittently, when the occupant is looking in a direction of a camera, across a plurality of devices within the vehicle;

interpolating, using one or more processors, mental state data in between the collecting which is intermittent, wherein the intermittent mental state data is interpolated to fill in gaps in the collected mental state data;

obtaining analysis of the mental state data on the vehicle occupant, wherein the analysis of the mental state data includes analyzing the mental state data that was interpolated; and rendering an output based on the analysis of the mental state data, wherein the rendering includes communicating with a navigation component of the vehicle.

27. A computer system for mental state analysis comprising:

a memory which stores instructions;

one or more processors attached to the memory wherein the one or more processors, when executing the instructions which are stored, are configured to:

collect mental state data of a vehicle occupant within a vehicle on an intermittent basis wherein the mental state data includes facial image data and the facial image data is collected intermittently, when the occupant is looking in a direction of a camera, across a plurality of devices within the vehicle;

interpolate, using one or more processors, mental state data in between the collecting which is intermittent, wherein the intermittent mental state data is interpolated to fill in gaps in the collected mental state data;

obtain analysis of the mental state data on the vehicle occupant, wherein the analysis of the mental state data includes analyzing the mental state data that was interpolated; and render an output based on the analysis of the mental state data, wherein rendering includes communicating with a navigation component of the vehicle.

* * * * *